(12) United States Patent
Purdy et al.

(10) Patent No.: US 7,011,647 B2
(45) Date of Patent: Mar. 14, 2006

(54) INTRODUCER SHEATH

(75) Inventors: Phillip D. Purdy, Dallas, TX (US);
Ajit Nair, Fremont, CA (US); Pete Phong Pham, Fremont, CA (US);
Kamal Ramzipoor, Fremont, CA (US);
Mehran Bashiri, San Carlos, CA (US);
Joseph C. Eder, Los Altos Hills, CA (US)

(73) Assignees: SciMed Life Systems, Inc., Maple Grove, MN (US); Board of Regents, The University of Texas System, Austin, TX (US)

( * ) Notice: Subject to any disclaimer, the term of this patent is extended or adjusted under 35 U.S.C. 154(b) by 290 days.

(21) Appl. No.: 10/328,349

(22) Filed: Dec. 23, 2002

(65) Prior Publication Data

US 2003/0130577 A1    Jul. 10, 2003

Related U.S. Application Data

(63) Continuation-in-part of application No. 09/905,670, filed on Jul. 13, 2001.

(51) Int. Cl.
A61M 5/178    (2006.01)
A61M 25/01    (2006.01)

(52) U.S. Cl. .................. 604/164.04; 604/525

(58) Field of Classification Search ............ 604/95.03, 604/96.01, 158, 161, 164.01, 164.02, 164.03, 604/164.04, 164.07, 164.1, 174, 264, 523, 604/524, 525; 606/191, 192, 194
See application file for complete search history.

(56) References Cited

U.S. PATENT DOCUMENTS 3,782,388 A    1/1974    Page
4,619,643 A    10/1986   Bai
4,737,146 A *  4/1988    Amaki et al. ............... 604/512
4,808,157 A    2/1989    Coombs
4,838,878 A    6/1989    Kalt et al.
4,904,237 A    2/1990    Janese
4,911,163 A    3/1990    Fina
4,950,232 A    8/1990    Ruzicka et al.
4,973,305 A    11/1990   Goltzer
5,085,631 A    2/1992    Leighton
5,098,393 A    3/1992    Amplatz et al.

(Continued)

FOREIGN PATENT DOCUMENTS

DE    37 26 453    2/1989

(Continued)

OTHER PUBLICATIONS

Amar et al., "Microcatheterization of the cervical epidural space via lumbar puncture: Technical note," *Neurosurgery*, 48(5):1183-1187, 2001. Article from the Neurosurgery website at: http://www.neurosurgery-pnline.com, Oct. 23, 2001.

(Continued)

Primary Examiner—Nicholas D. Lucchesi
Assistant Examiner—Mark K Han
(74) Attorney, Agent, or Firm—Crompton, Seager & Tufte, LLC

(57) ABSTRACT

A variety of devices for use in accessing the subarachnoid space are described. In several embodiments an introducer sheath is disclosed having three main sections, a distal portion, an intermediate portion, and a proximal portion. The distal portion and intermediate portion form a first bend, and the intermediate portion and the proximal portion form a second bend, giving the overall device a general L-shape, S-shape, C-shape, or a three dimensional Z-shape. Apparatuses for attaching an introducer sheath to the skin of a patient are also discussed, as are methods for using, shaping and sizing an introducer sheath.

62 Claims, 9 Drawing Sheets

U.S. PATENT DOCUMENTS

| | | | |
|---|---|---|---|
| 5,160,323 | A | 11/1992 | Andrew |
| 5,256,146 | A | 10/1993 | Ensminger et al. |
| 5,297,564 | A | 3/1994 | Love |
| 5,378,241 | A | 1/1995 | Haindl |
| 5,385,152 | A | 1/1995 | Abele et al. |
| 5,397,305 | A | 3/1995 | Kawula et al. |
| 5,423,849 | A | 6/1995 | Engelson et al. |
| 5,445,625 | A | 8/1995 | Voda |
| 5,449,343 | A | 9/1995 | Samson et al. |
| 5,470,318 | A | 11/1995 | Griffith, III et al. |
| 5,478,331 | A | 12/1995 | Heflin et al. |
| 5,520,647 | A | 5/1996 | Solar |
| 5,542,936 | A | 8/1996 | Razi |
| 5,613,950 | A | 3/1997 | Yoon |
| 5,630,802 | A | 5/1997 | Moellmann et al. |
| 5,637,098 | A * | 6/1997 | Bierman .................... 604/180 |
| 5,704,915 | A | 1/1998 | Melsky et al. |
| 5,738,650 | A | 4/1998 | Gregg |
| 5,810,869 | A | 9/1998 | Kaplan et al. |
| 5,814,016 | A | 9/1998 | Valley et al. |
| 5,830,188 | A | 11/1998 | Abouleish |
| 5,833,632 | A | 11/1998 | Jacobsen et al. |
| 5,846,226 | A | 12/1998 | Urmey |
| 5,908,385 | A | 6/1999 | Chechelski et al. |
| 5,928,155 | A | 7/1999 | Eggers et al. |
| 5,928,260 | A | 7/1999 | Chin et al. |
| 5,931,810 | A | 8/1999 | Grabek |
| 5,935,122 | A | 8/1999 | Fourkas et al. |
| 5,951,520 | A | 9/1999 | Burzynski et al. |
| 5,980,480 | A | 11/1999 | Rubenstein et al. |
| 5,980,484 | A | 11/1999 | Ressemann et al. |
| 5,980,504 | A * | 11/1999 | Sharkey et al. ............. 604/510 |
| 6,004,295 | A | 12/1999 | Langer et al. |
| 6,026,316 | A | 2/2000 | Kucharczyk et al. |
| 6,036,654 | A | 3/2000 | Quinn et al. |
| 6,061,587 | A | 5/2000 | Kucharczyk et al. |
| 6,080,140 | A | 6/2000 | Swaminathan et al. |
| 6,086,548 | A * | 7/2000 | Chaisson et al. ........... 600/585 |
| 6,090,072 | A | 7/2000 | Kratoska et al. |
| 6,120,499 | A | 9/2000 | Dickens et al. |
| 6,129,713 | A | 10/2000 | Mangosong et al. |
| 6,146,354 | A | 11/2000 | Beil |
| 6,162,170 | A | 12/2000 | Foley et al. |
| 6,168,588 | B1 * | 1/2001 | Wilson ....................... 604/525 |
| 6,183,443 | B1 | 2/2001 | Kratoska et al. |
| 6,190,349 | B1 | 2/2001 | Ash et al. |
| 6,200,336 | B1 | 3/2001 | Pavcnik et al. |
| 6,214,029 | B1 | 4/2001 | Thill et al. |
| 6,251,115 | B1 | 6/2001 | Williams et al. |
| 6,272,370 | B1 | 8/2001 | Gillies et al. |
| 6,293,924 | B1 | 9/2001 | Bagaoisan et al. |
| 6,319,241 | B1 | 11/2001 | King et al. |
| 6,352,530 | B1 | 3/2002 | Mangosong |
| 6,379,331 | B1 | 4/2002 | Barbut et al. |
| 6,673,999 | B1 * | 1/2004 | Wang et al. .................. 174/36 |
| 6,699,269 | B1 | 3/2004 | Khanna |
| 2002/0091356 | A1 | 7/2002 | Barbut et al. |

FOREIGN PATENT DOCUMENTS

| | | |
|---|---|---|
| EP | 0 454 264 | 10/1991 |
| EP | 1 062 959 | 12/2000 |
| WO | WO 97/44082 | 11/1997 |
| WO | WO 98/38953 | 9/1998 |
| WO | WO 98/57603 | 12/1998 |
| WO | WO 99/20334 | 4/1999 |
| WO | WO 00/51669 | 9/2000 |
| WO | WO 01/54766 | 8/2001 |
| WO | WO 02/068036 | 9/2002 |

OTHER PUBLICATIONS

Blomberg, "A method for epiduroscopy and spinaloscopy. Presentation of preliminary results," *Acta Anaesthesiol. Scan.*, 29(1):113-116, 1985.

Blomberg, "Fibrous structures in the subarachnoid space: a study with spinaloscopy in autopsy subjects," *Anesth. Analg.*, 80(5):875-879, 1995.

Delhaas, "Extradural and subarachnoid catheterization using the Seldinger technique," *Br. J. Anaesth.*, 76(1):149-150, 1996.

Eguchi et al., "Endoscopy of spinal cord and posterior fossa by a lumbar percutaneous approach: endoscopic anatomy in cadavers," *Minim. Invasive Neurosurg.* 42(2):74-78, 1999.

Eguchi et al., "Endoscopy of the spinal cord: cadaveric study and clinical experience," *Minim. Invasive Neurosurg.*, 42 (3):164-151, 1999.

Fries et al., "Biportal Neuroendoscopic Microsurgical Approaches to the study of Subarachnoid Cisterns. A Cadaver Study," *Minim Invas. Neurosurg.*, 39(4):99-104, 1996.

Hamada et al., "Microcatheter intrathecal urokinase infusion into cisterna magna for prevention of cerebral vasospasm," *Stroke*, 31:2141-2148, 2000.

Karakhan et al., "Operative spinal endoscopy: stereotopography and surgical possibilities," *Acta. Neurochir. Suppl.*, 61:108-114, 1994.

Karakhan, "Use of intracranial endoscopy in morphologic studies," *Arkh. Anat. Gistol. Embriol.*, 98(1):75-82, 1990. Russian.

Miyamoto et al., "The development of spinal endoscope using a flexible optic fiber," *No. To. Shinkei*, 41(12):1233-1238, 1989. Abstract on p. 1238.

Stefanov et al., "A new method for transcutaneous coaxial neuroendoscopy," *Anat. Embryol.*, 194(4):319-326, 1996.

Suzukawa et al., "Percutaneous fiberoptic spinal laser endoscopy," *J. Clin Laser Med Surg.*, 8(6):27-30, 1990.

Tanaka et al., "Endoscopic treatment of symptomatic spinal subarachnoid cysts," *AJR Am. J. Roentgenol.*, 169(6):1719-1720, 1997.

Uchiyama et al., "Ultrafine Flexible Spinal Endoscope (Myeloscope) and Discovery of an Unreported Subarachnoid Lesion," *Spine*, 23(21):2358-2362, 1998.

Vinas et al., "Microanatomical basis for the third ventriculostomy," *Minim. Invasive Neurosug.*, 39(4):116-121, 1996.

Document depicting a prototype stent, sent to applicant on Jul. 13, 2001.

"Back Break," Article from *Forbes Magazine*, p. 123-124, Aug. 12, 2002.

"Keeping it Cool," Article from *Health Communities, United Hospital*, 11(1):1, 8, Winter 2003.

* cited by examiner

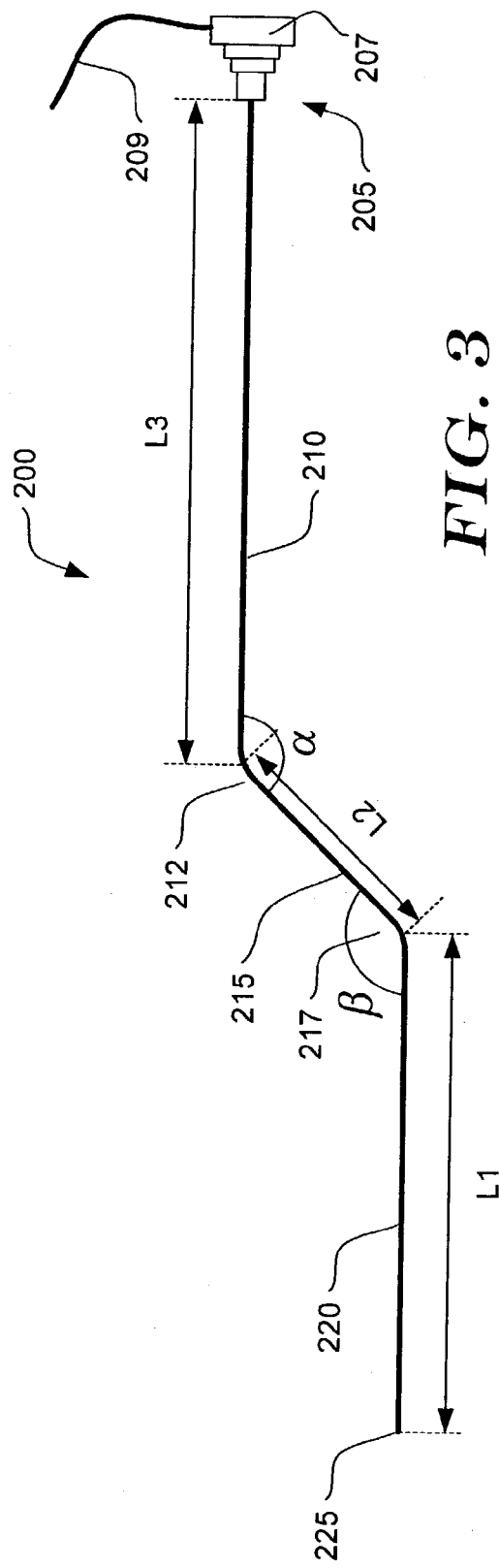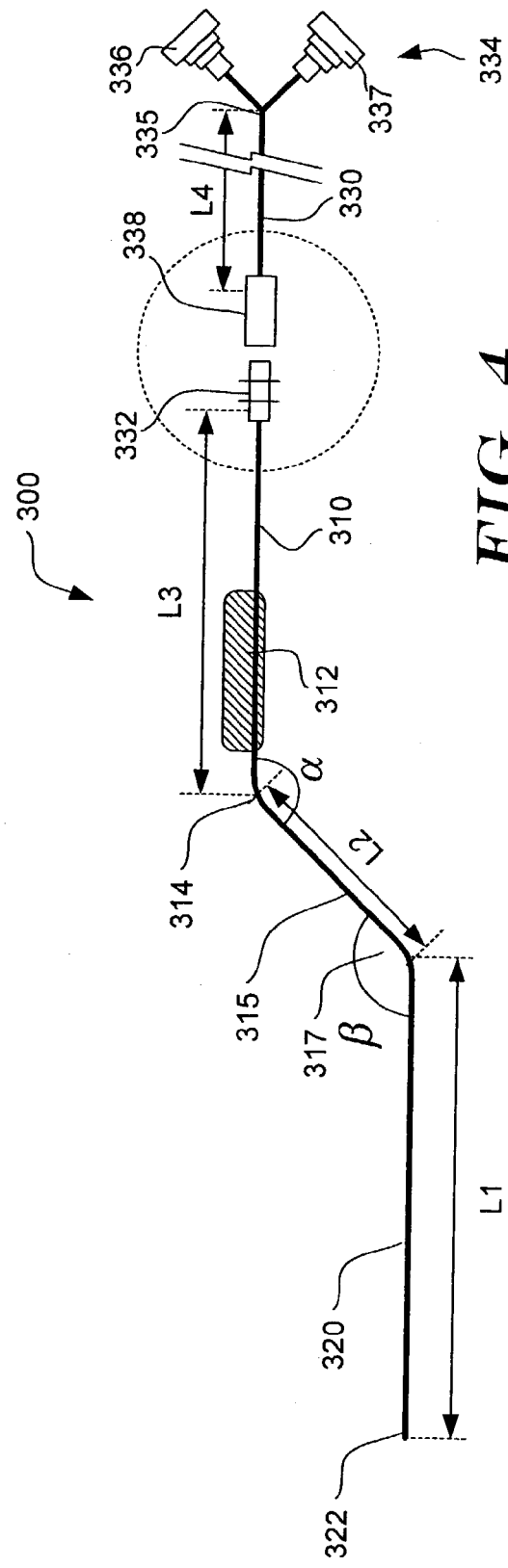
FIG. 3
FIG. 4

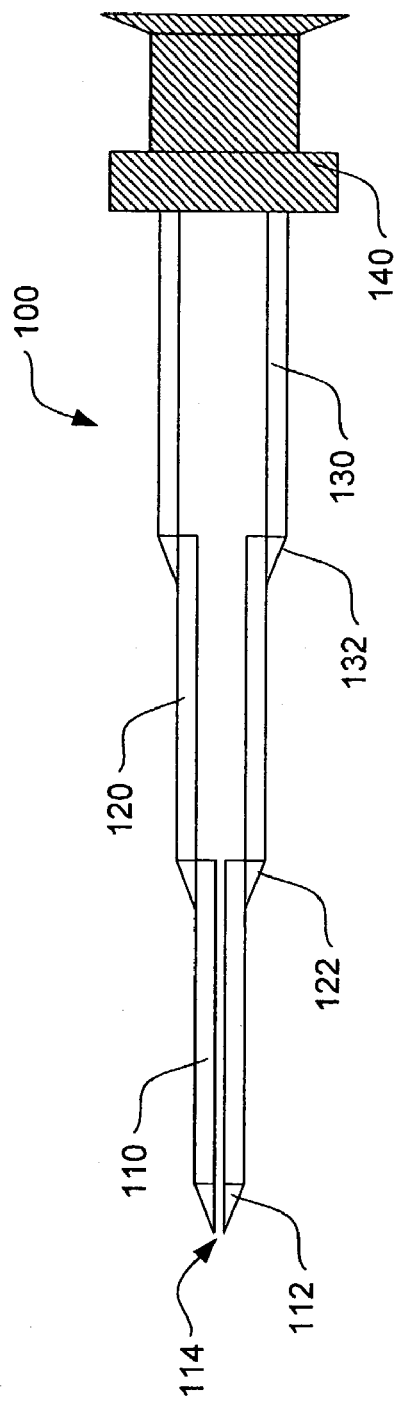
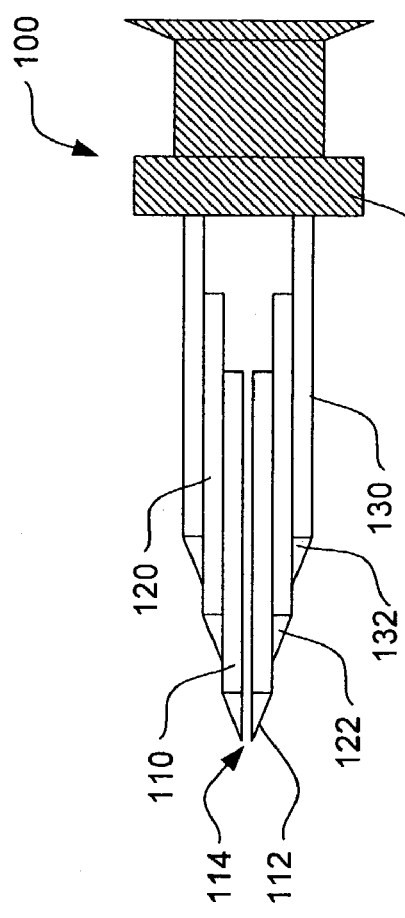
FIG. 19A
FIG. 19B

INTRODUCER SHEATH

RELATED APPLICATIONS

This is a continuation-in-part of co-pending application Ser. No. 09/905,670 Filed Jul. 13, 2001 entitled METHODS AND APPARATUSES FOR NAVIGATING THE SUBARACHNOID SPACE, which is incorporated herein by reference.

TECHNICAL FIELD

The present invention relates generally to devices and methods for accessing the subarachnoid space. More particularly, it relates to devices and methods for using an introducer for accessing the subarachnoid space.

BACKGROUND

Historically, brain neurosurgery has begun with entry into the cranium by removal of parts of the bones making up the skull while performing a craniotomy. Removal of parts of the skull allows access to areas of the brain, and careful manipulation of tissue has even allowed access to structures deep within the brain. Recently, magnetic resonance imaging (MRI) has proved a useful method for viewing structures of the brain and has been included in some such procedures. However, one difficulty that has arisen is that, while the MRI can provide excellent images, the bulky MRI machines in use do not allow the surgeon to perform a procedure while viewing a changing or real-time image. Further, access to deeper structures creates a variety of risks caused by the manipulation of the soft tissues of the brain. An alternative to craniotomy could help with these difficulties.

One alternative method of accessing the inner areas of the brain that has recently arisen is through vascular catheterization and advancement into areas of the brain. The methods enable different treatment and analysis options that may supplement or replace those offered by craniotomy. However, these methods are limited to areas accessible using vascular passageways. Further, with respect to introducing drugs or other substances, the transfer of some substances, for example some proteins, across the barriers between blood and the cerebrospinal fluid (CSF), is not allowed by the biological mechanisms that control the interaction of blood and CSF.

The subarachnoid space is a compartment that contains the body of the spinal cord and CSF, which is a fluid that fills and surrounds the ventricles of the brain and the spinal cord and acts as a lubricant and a mechanical barrier against shock. The spinal subarachnoid space is the part of the subarachnoid space containing the spinal cord and extending into the base of the brain cavity. This space may represent a viable nonvascular route to accessing the brain, providing an alternative to vascular catheterization and/or craniotomy. One method of using the subarachnoid space would be to introduce a catheter into the subarachnoid space and advance it to a chosen location along the spinal column, or, potentially, to enter the cranium and access the brain. Such methods are noted and discussed, along with a variety of potential treatment options, in U.S. patent application Ser. No. 09/905,670 entitled METHODS AND APPARATUSES FOR NAVIGATING THE SUBARACHNOID SPACE, which is expressly incorporated herein by reference.

With respect to catheterization, the MRI machine may create difficulties for procedures that would be desirable, for example, once the spinal subarachnoid space is accessed, it may be necessary to change catheters. To change catheters could require removing the patient from the MRI machine, increasing the time and difficulty of the overall operation. To make such changes easier, it would be helpful to use an introducer sheath that would enable several catheters to be introduced at once, or to enable a catheter to be removed and a different catheter to be introduced at the same location. However, conventional introducer sheaths known for use in vascular procedures often extend a very short distance outside the patient's body, and so would be difficult to access while the patient, and hence the proximal end of the introducer sheath, is in an MR imaging device.

An introducer sheath for use with entry into the spinal subarachnoid space should provide access past the bones of the spine. Introducer sheaths for use in vascular catheterization are designed to enter arteries not protected by such protective bony surroundings. New introducer sheath geometries may be useful to address these problems.

SUMMARY OF SEVERAL EMBODIMENTS

To address these possibilities, some embodiments of the present invention include an introducer sheath adapted for use in accessing the spinal subarachnoid space. In one embodiment, the introducer sheath includes a geometric design resembling the shape defined by a pathway leading through an interspace between two vertebrae and into the spinal subarachnoid space of a patient. In such embodiments, the shape includes a shaped portion generally resembling a curved L-shape. In some embodiments, the shape is defined by a pathway leading through an interspace between two vertebrae and along the skin on the back of a patient.

In some embodiments, the geometric design resembles the shape defined by the pathway leading from the spinal subarachnoid space, through an interspace between two vertebrae, and along the skin on the back of a patient. In some such embodiments, the introducer sheath includes a geometric design resembling a double curve or S-shape. In another embodiment, the sheath may be provided in a default shape, but can be adjusted, for example, by warming the sheath material and applying pressure to adapt the sheath to the particular anatomy of a patient.

In some embodiments the introducer sheath includes a first section, and a second section, the first section and second section forming an angle such that when the sheath is placed in the anatomy of a patient, the first section can extend within the spinal subarachnoid space, and the second section can extend through an interspace between two vertebrae of a patient. In some embodiments, the angle formed by the first section and the second section is in the range of about 60–180 degrees. In some embodiments, the second section has a length that is adapted to extend from the spinal subarachnoid space to the surface of the skin of a patient through an interspace between two vertebrae of the patient.

Several embodiments include a third section, and the second section and third section form an angle such that when the sheath is placed in the anatomy of a patient, the second section can extend through an interspace between two vertebrae of a patient, and at least a portion of the third section can extend externally from the patient, for example, along the skin on the back of a patient. In some embodiments, the angle formed by the second section and the third section is in the range of about 30–170 degrees. In one embodiment, the first section can be inserted inside the body of the patient, while the third section remains outside the patient's body, and the second section connects the first section to the third section. In some embodiments, the introducer sheath is adapted and configured with appropriate angles and lengths of the sections such that, when the first section extends within the spinal suabarachnoid space, at least a portion of the third section extends adjacent the skin of the patient.

Some embodiments include one or more sensing devices disposed on a distal portion of the introducer sheath. In at least one embodiment, a temperature sensor, which may be a wired or wireless transducer, is embedded or attached to a wall of the introducer sheath at a location which will, when the sheath is introduced into a patient's subarachnoid space, be disposed within the subarachnoid space as well. In another embodiment, a pressure sensor is embedded or attached to a wall of the introducer sheath in similar fashion. The pressure sensor may be used to monitor the pressure of the CSF in at least some embodiments.

The introducer sheath may include one or more valves, for example, a hemostatic or other non-return valve. Such valves are included in one embodiment to help isolate bodily fluids and prevent leakage from the spinal subarachnoid space as well as, conversely, to prevent foreign particles from entering the subarachnoid space via the introducer sheath. In another embodiment, the introducer sheath includes an attachment pad for securing the introducer sheath to a patient's skin. Such attachment pads may include features to improve patient comfort and allow for patient movement during a procedure. In yet another embodiment, the introducer sheath includes suture hooks or suture holes that allow a surgeon to suture the introducer sheath to the patient's skin.

Several embodiments include aspects that aid compatibility of the introducer sheath with imaging techniques, for example MR imaging techniques, and the like, or others. One such embodiment includes an introducer sheath made of non-magnetically reactive materials desired for compatibility in an MR imaging system. Another embodiment includes a third section (the portion outside the patient's body) which extends well away from the point of entry into the patient's body, allowing a doctor to access the introducer sheath even while the patient is inside an MR imaging system. Yet another embodiment includes the use of connector valves, such as a Leur valve, or the like, at the proximal end of the introducer sheath to allow additional lengths to be added to the introducer sheath.

In several embodiments, the sizes, shapes, and angles between sections or portions of the introducer sheath may be chosen to correspond to the anatomy of a patient and/or the needs of a procedure.

BRIEF DESCRIPTION OF THE DRAWINGS

FIG. 3 is a schematic side view of an illustrative embodiment showing an introducer sheath;

FIG. 4 is a schematic side view of another illustrative embodiment showing an introducer sheath;

FIGS. 19A and 19B are cross sectional views of an illustrative dilator in extended and contracted positions which may be used with several embodiments.

DETAILED DESCRIPTION OF SEVERAL ILLUSTRATIVE EMBODIMENTS

The following detailed description should be read with reference to the drawings. The drawings, which are not necessarily to scale, depict illustrative embodiments and are not intended to limit the scope of the invention.

For many embodiments suggested herein, the introducer sheath may presumed to be made of material and structure compatible with certain imaging techniques, for example an MRI scanning compatible material or structure. For example, ferrous materials, such as some stainless steel alloys often used to provide braided reinforcement to catheters, are typically magnetically responsive, and are generally not used in conjunction with MRI equipment, or are provided with structure that would render them compatible with MRI equipment. However, as imaging technologies continue to evolve, it may become possible to use a wider range of materials, including magnetically reactive materials, in devices for introduction into the subarachnoid space. Additionally, in embodiments not intended for use with MR imaging, a wide range of material and structures, including magnetically reactive materials, may be used. For at least some embodiments, though, material and structure selection aimed at assuring MR imaging compatibility remains a consideration. The selection of materials for use in an introducer sheath, however, should not be seen as a limitation on the present invention. One of skill in the art can readily appreciate that there are a wide variety of potential materials that may be used to facilitate the present invention. When the time arises where imaging technologies change, broadening material compatibility, other materials may be used in accordance with the present invention without changing the inventive concept. Additionally, materials and structures that aid in imaging may be incorporated into the sheath.

An additional note with respect to the following description is that, while the introducer sheath is described in terms of different sections with bends therebetween, the sheath may be made as a single element, for example, through extrusion molding and the like. Variations in sizes and flexibility, as well as the inclusion of rigid or semi-rigid bends, should not be interpreted as requiring a certain method or type of construction. While the present description is written largely in terms of use in a human patient, the present invention may also be used with other vertebrate organisms, for example in veterinary procedures by applying adaptations suited to a particular organism's anatomy.

Also, as used herein, the term "about" applies to all numeric values, whether or not explicitly indicated. The term "about" generally refers to a range of numbers that one of skill in the art would consider equivalent to the recited values (i.e. having the same function or result). In many instances the term "about" may include numbers that are rounded to the nearest significant figure.

Figure 1:
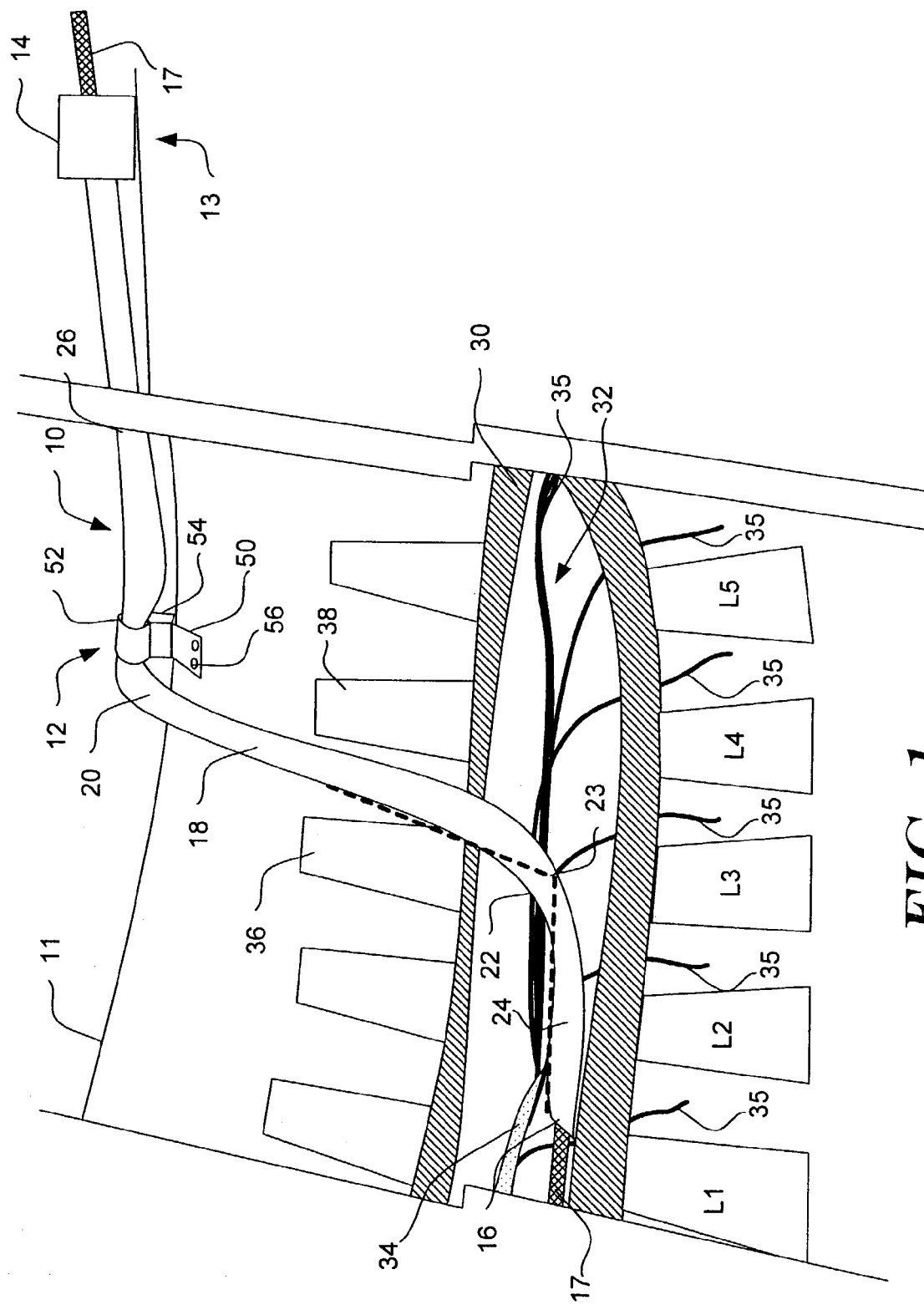
FIG. 1 is a diagrammatic side view of entry of an introducer sheath including a catheter therethrough into the spinal subarachnoid space.

FIG. 1 is a diagrammatic side view of entry of an illustrative embodiment of an introducer sheath including a catheter therethrough into the spinal subarachnoid space 32. In FIG. 1, introducer sheath 10 penetrates skin 11 and includes attachment apparatus 12 on skin 11, proximal end member 14 above skin 11, and distal end 16 below skin 11. An intermediate portion 18 appears between first bend 20 and second bend 22. A distal portion 24 is between the distal end 16 and second bend 22, while a proximal portion 26 is between first bend 20 and proximal end member 14.

The insertion of introducer sheath 10 through skin 11 and into spinal subarachnoid space 32 may be performed in a variety of ways. Prior to percutaneously introducing sheath 10 into subarachnoid space 32, an operator may direct a guidewire through skin 11 and dural membrane 30 and into subarachnoid space 32, in order to facilitate the introduction of sheath 10. This guidewire introduction may be achieved, for example, by directing a needle through the skin 11 and the dural membrane 30 between any of the lumbar vertebrae.

With a needle in place, a guidewire may be introduced into the spinal subarachnoid space through a lumen within the needle. The guidewire may then be directed superiorly and advanced within the spinal subarachnoid space and toward the patent's head to a desired location, while in other embodiments, the guidewire may be directed inferiorly and advanced within the spinal subarachnoid space away from the patient's head. The position of the guidewire within the patient, including within the various regions of the subarachnoid space, may be monitored using any suitable imaging modality, such as magnetic resonance imaging, fluoroscopy, endoscopy, computed tomography, thermal imaging, sonography, or any combination of these. Moreover, these imaging modalities can be used throughout a procedure to monitor the various positions of other medical devices, provided that the right conditions exist (such as sufficient radiopacity, etc.).

After placement of a needle and advancement of a guidewire, the operator may dilate the tract created by the guidewire using one or more medical devices suited for that purpose, such as dilators. This may also be done after removing the needle. Alternatively, a suitably structured sheath may be introduced over the guidewire for the same dilation purpose and also to facilitate intracranial access with a second device introduced through the passageway of the sheath. If an operator uses a dilator, a medical device such as sheath 10 may be passed over the dilator, and the dilator can then be removed through the passageway of the sheath.

Referring now to FIGS. 19A–19B, an illustrative dilator is shown. Such a dilator 100 may be used with some embodiments of the present invention. FIG. 19A illustrates dilator 100 in an extended configuration, having movable portions 110, 120 and 130, and hub 140. The movable portions 110, 120, and 130, are not necessarily to scale, for example, in one embodiment the third portion 130 is substantially longer than the other two portions 110, 120. First portion 110 includes an angled tip 112 that may be adapted to facilitate insertion into an opening, for example, by placement of a guidewire through gap 114.

For example, an introducer sheath such as introducer sheath 10 shown in FIG. 1 may be initially disposed upon the dilator 100 such that the proximal end 13 of introducer sheath 10 (FIG. 1) is adjacent to hub 140 (FIG. 19A), with most if not all of the sheath disposed upon the third portion 130. A guidewire may be introduced over or through a puncture needle in a standard spinal puncture, and the proximal end of the guidewire may be passed through the gap 114, and, in some embodiments, through a lumen in the hub 140, which may include or be connected to a non-return valve. The dilator 100 is then advanced such that the initial opening provided by a needle is expanded. During advance of the dilator 100, the movable portions 110 may retract until they are disposed generally as shown in FIG. 19B, with the angled tip 112 and angled intermediations 122, 132 providing a smoothed surface that does not present a "shoulder" or ridge which may cause unnecessary trauma during dilation. The dilator 100 is shown merely for purposes of illustrating one method of advancing the introducer sheath 10 (FIG. 1) through a space between bony structures 36, 38 (FIG. 1), and should not be interpreted as limiting either structures or methods disclosed herein. Other dilators, such as a dilator incorporating an inflatable member, such as a balloon dilation catheter, or other dilation structure may be used.

Referring again to FIG. 1, in some embodiments, the distal portion 24 is more flexible or softer than the intermediate portion 18, while the intermediate portion 18 may be stiffer to maintain a position between vertebrae. The proximal portion 26 may have varying or even arbitrary stiffness in some embodiments. Certain sections of the proximal portion 26 may be chosen in some embodiments to be stiffer than others, for example, in one embodiment the proximal portion is relatively stiff between the attachment apparatus 12 and the intermediate portion 18 to maintain relative positioning. Alternatively, in another embodiment, there may be extra flexibility between attachment apparatus 12 and intermediate section 18 to allow for patient movement, for example, due to movements such as breathing or even, in one embodiment, stimulus causing muscle contraction applied intentionally or unintentionally by introduction of devices into the subarachnoid or intracranial spaces.

Figure 2:
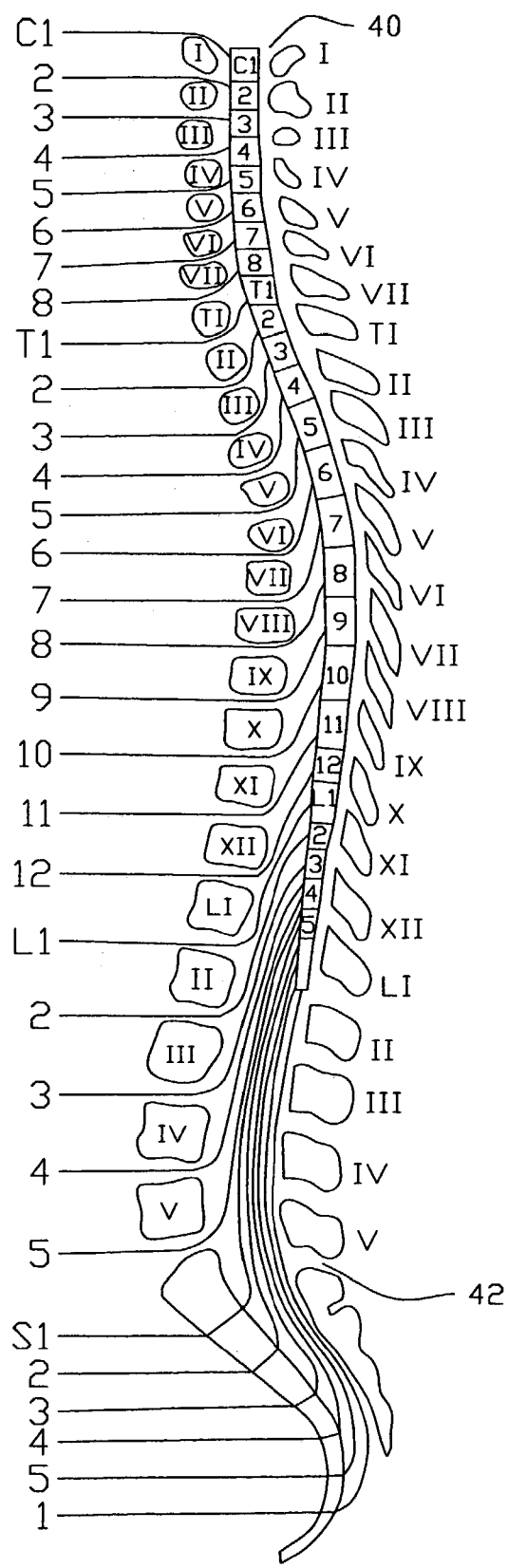
FIG. 2 is a depiction of the spinal column and vertebrae of an adult human being.

The intermediate portion 18 of introducer sheath 10 crosses dural membrane 30, penetrating the dural membrane 30 to enter subarachnoid space 32 which includes spinal cord 34. Spinal cord 34 terminates approximately even with lumbar L1, and spinal nerves 35 extend further along subarachnoid space 32. The intermediate portion 18 crosses between bony structures 36 and 38, which represent the third and fourth lumbar vertebrae. The gap between bony structures 36 and 38 is known as an interspace. Interspaces appear between each of the vertebrae including the cervical, thoracic and lumbar vertebrae, as shown in FIG. 2, which is a representation of the spinal column and vertebrae of an adult human. Though introducer sheath 10 is shown in FIG. 1 as penetrating the dural membrane 30 between lumbar vertebrae 36 and 38, any of the interspaces shown in FIG. 2, from the interspace appearing above cervical vertebrae number one 40 all the way down to the interspace below lumbar vertebrae number five 42 could also be penetrated.

The interspace selected for insertion of the introducer sheath 10 can play a role in determining the lengths of the distal portion 24, intermediate portion 18 and proximal portion 26 as well as the angles and sizes of first and second bends 20, 22. For example, as can be seen from FIG. 2, which is illustrative of a typical adult human, the alignment, separation and angle of the vertebrae with respect to one another varies along the length of the spine. The lengths and bend angles may thus be adapted for the particular interspace chosen. Additionally, the outer diameter of the distal portion 24 and the intermediate portion 18 may be adapted for entry into a particular interspace, as the allowed outer diameters for entry may vary from one interspace to the next, as well as from one patient to the next. For example, in some embodiments it may be useful to access the pia mater surrounding the brain, which would be superior to the first cervical vertebra 40, with a device of an outer diameter requiring at least a certain value so that entry through a lumbar interspace is called for; thus, the length of distal portion 24 may be chosen so that the distal end 16 is adjacent to the pia mater when the intermediate portion 18 is between L3 and L4.

First bend 20 can be adapted to direct intermediate section 18 between bony structures 36, 38, and generally direct the distal portion 24 into the spinal subarachnoid space. Depending upon the individual anatomy of a patient and the interspace chosen for entry into the subarachnoid space, first bend 20 may vary significantly, as noted further below with respect to FIGS. 3 and 4. Intermediate section 18 may also vary in length depending again on the interspace selected and the particular anatomy of the patient. Likewise, second bend 22 may vary depending upon the interspace selected and the particular anatomy of the patient. For the purposes of illustration, bends 20, 22 will be discussed below in terms of rather exact angles, and treated as if a single location defines the angle. However, it should be understood from FIG. 1 that the bends 20, 22 provided in introducer sheath 10 are, in most embodiments, gradual turns, rather than sharp angles. Thus, while second bend 22 is described in terms of an angle defined by dotted line 23, it is to be understood that a curve or bend, rather than an exact, sharp angle is meant. For example, in some embodiments, first bend 20 or second bend 22 may be effected across a length of about one-half to seven centimeters, while in other embodiments the bends may be effected across about three to five centimeters of the proximal portion 26 or distal portion 24, respectively, though greater or lesser length can be used in other embodiments. In other embodiments, the bends 20, 22 may be more abrupt, and may even be sharp turns, though material making up the bends may be smoothed to reduce tissue irritation potentially caused by sharp angles.

Distal portion 24 may vary widely in length. In some embodiments, distal portion 24 extends in the range of about ten centimeters into spinal subarachnoid space 32. However, in other embodiments distal portion 24 may range in length from about one centimeter up to as much as seventy centimeters, for example, one embodiment contemplates a distal portion of length in the range of up to five centimeters, for example, in the range of three and five centimeters, while another embodiment contemplates a length in the range of about twenty-five to fifty centimeters. Intermediate portion 18 can vary in length as well, but may be adapted for entry into a particular interspace. In some embodiments, the intermediate portion 18 can have a length in the range of about two to about twelve centimeters, or in the range of about five to seven centimeters, though greater or lesser length can be used in other embodiments. Meanwhile, proximal portion 26 may vary widely in length as well. In some embodiments, the proximal portion 26 may be integral to skin attachment apparatus 12, which in turn connects directly to second bend 22 on one end and proximal end member 14 on the other end. In other embodiments, proximal portion 26 may extend in a range of up to thirty and even ninety centimeters, or longer. Some embodiments use minimum lengths for the proximal portion of five centimeters or thirty centimeters, depending at least in part upon the needs of the patient and physician, for example, if a single suture pad attachment is to be used, a shorter proximal portion may be used. The proximal portion 26 may be selected to have a length allowing a physician to access the proximal end member 14 from outside an imaging device or machine, for example an MRI machine, while a patient is in a position to have images taken and has the introducer sheath 10 inserted into the spinal subarachnoid space.

Attachment apparatus 12 can be included to secure introducer sheath 10 to skin 11, but may be omitted in other embodiments. In the illustrative embodiment shown, attachment apparatus 12 includes flap 50 and cuff 52, with a spacer 54 therebetween. Flap 50 is used to provide direct attachment to the skin 11, including, for the illustrative embodiment shown, suture holes 56 through which sutures may be placed to secure flap 50. Spacer 54 may enclose a pad such as a sponge or foam, used to increase patient comfort. Cuff 52 may be fixed to introducer sheath 10 at a permanent location, or the introducer sheath 10 may be slidably disposed within cuff 52.

The distal end 16 of introducer sheath 10 may be angled or tapered as shown or otherwise adapted to facilitate insertion through skin 11 and dural membrane 30. Distal portion 24 may be made of a softer or more flexible material than the intermediate section 18. Distal end 16 or distal portion 24 (as well as the rest of introducer sheath 10, as desired) may also include a marker or coating to enhance its imaging visibility, for example MRI visibility, and, for some embodiments, may include radiopaque materials or other high visibility materials adapted for use with other imaging technologies. In one embodiment, the distal end 16 may include a marker or coating of extracellular Gadolinium, for example, or may include dysprosium in a marker or coating.

Introducer sheath 10 includes a lumen extending from distal end 16 to proximal end member 14. As shown, a catheter 17 has been inserted through the entire lumen. While catheter 17 is shown exiting at the proximal end 13 and distal end 16 of the introducer sheath 10, either location may be changed. Catheter 17 could exit the introducer sheath at a point proximal the distal end 16 inside the subarachnoid space, for example, through an opening in the side of the introducer sheath. Also, though only one catheter 17 is shown, in some embodiments, more than one catheter could be inserted through the same introducer sheath. The proximal end member 14 may be a manifold or entry point for catheters, endoscopes, guide wires, flush tubes and other devices, and the sheath 10 may include a lumen for passing any of these.

The introducer sheath 10 may define a lumen extending from the distal portion 24, and in some embodiments, the distal end 16, to the proximal portion 26, and in some embodiments, the proximal member 14. Following are some size parameters for several illustrative embodiments, however, lumen and outer diameter sizes both larger and smaller may be substituted. In some embodiments, the lumen in the distal portion 24 may have a diameter of in the range of about 0.1 to 3 millimeters, and in some embodiments, in the range of about 0.2 to 3 millimeters, though other diameters can be used in other embodiments. In some embodiments, the outer diameter of the distal portion 24 may range from about 0.2 to 6 millimeters, 0.2 to 4 millimeters and in some embodiments, in the range of about 1 to 4 millimeters, though other diameters can be used in other embodiments. The lumen in the intermediate portion 18 may be similarly sized to that of the distal portion 24, as may the lumen in the proximal portion 26.

With respect to the proximal portion 26, it is possible to have an even larger lumen to make the lumen more easily passed. For example, because the proximal portion 26 is not inserted into the body of the patient the outer diameter of the proximal portion 26 is not subject to the anatomical limits of a patient into whom the sheath is inserted, and hence there are no anatomical limits on the inner lumen diameter in the proximal portion 26, either. The lumen and outer diameter of the intermediate portion 18 and distal portion 24 may be sized to adapt to the particular interspace selected for insertion. For example, the interspace width or area available for insertion may vary from the lumbar region to the cervical region of the spine, and it may also vary from patient to patient.

An additional feature of the proximal portion 26 provided in some embodiments is that the outer surface may be treated, contoured or patterned to enable an attachment apparatus 12 to selectively prevent longitudinal motion of the proximal portion 26. In this document, the term "longitudinal" should be understood to mean in a direction corresponding to an elongated direction of the introducer 10.

Distal portion 24 and distal end 16 may include a transducer 27. The transducer 27 may be, for example, a microsensor embedded into a wall of sheath 10 for sensing the temperature, pressure, body chemistry or the like inside the subarachnoid space 32. The transducer 27 may be coupled to an electric (i.e. a wire) or optic connection running along, through, or embedded into sheath 10 from a distal location to a proximal location. In other embodiments, the transducer 27 may be a wireless sensor, for example, a wireless resonant pressure or temperature sensor. The transducer 27 may be included for determining a physiologic property during an operation, or to assist in diagnosis.

In some embodiments, the transducer 27 may be advanced to a location in the subarachnoid space via entry into the spinal subarachnoid space (e.g. through an interspace between two vertebrae). In other embodiments, the transducer may be provided on an introducer sheath adapted for entry through other access, for example, by access through a burr hole in the cranium, or any other means of entry into the subarachnoid space. This may include entry through a burr hole to access the ventricles or other areas of the brain. The sheath may be used, for example as a ventriculostomy catheter, including a transducer 27 adapted for use as a pressure transducer.

For example, one potential application may be in CSF cooling, where a device is introduced to the subarachnoid space to induce localized hypothermia. For such an operation, the transducer 27 may be a temperature sensor included to assist in monitoring the CSF temperature. Examples of GSF and tissue cooling are discussed in copending U.S patent application Ser. No. 10/328,560 filed on even date herewith entitled METHODS AND APPARATUSES FOR NAVIGATING THE SUBARACHNOID SPACE, which is incorporated herein by reference.

In another embodiment, the transducer 27 may be a pressure sensor for measuring the pressure of the CSF. A pressure sensor disposed in this manner could greatly simplify previous procedures which often involved the insertion of a drainage tube connected to a manometer. A pressure sensor used as the transducer 27 could not only simplify measurements of CSF pressure, it could also make such measurements more sanitary, safe, and accurate. Pressure measurement, or measurement of any other physiologic or biometric characteristic, may be performed in this fashion on its own, or as part of another procedure. Also, because the transducer 27 may be a microsensor embedded in wall of the sheath 10, it is possible to continue sensing CSF pressure while a second intraspinal or intracranial procedure is performed without interfering with the second procedure. Any of a wide variety of small sensing devices may be used as transducer 27 including, for example, resonant sensors, micromachined sensors, or even more conventional sensors which, though relatively bulky, may be inserted into the spinal subarachnoid space in lower regions where anatomy allows.

In some embodiments, the sheath 10 may include the transducer 27 embedded near the distal end of the sheath 10. In at least one such embodiment, the sheath 10 is sized with a sufficient length to be advanced until the transducer 27 is placed within a patient's head or ventricular system. In other embodiments the sheath 10 may be sized and adapted for advancement into the intracranial space until the transducer 27 is situated for sensing the CSF pressure or some other biometric or chemical property in the lateral ventricles or the third or fourth ventricals.

A wide variety of materials may be used to make the introducer sheath 10. For example, the introducer sheath 10 can be manufactured from any suitable material to impart the desired characteristics. Some examples of suitable materials can include, for example, polymers, metal-polymer composites, metals, metal alloys, or the like, or combinations or mixtures thereof. In some embodiments, consideration should be given to the MRI compatibility of the material chosen. Examples of other suitable materials include, but are not limited to, polymers such as polyoxymethylene, polybutylene terephthalate, polyether block ester, polyether block amide, fluorinated ethylene propylene, polyethylene, polypropylene, polyvinylchloride, polyurethane, polytetrafluoroethylene (PTFE), polyether-ether ketone, polyimide, polyamide, polyphenylene sulfide, polyphenylene oxide, polysufone, nylon, perfluoro(propyl vinyl ether), polyether-ester, polymer/metal composites, etc., or mixtures, blends or combinations thereof. One example of a suitable polyether block ester is available under the trade name ARNITEL, and one suitable example of a polyether block amide is available under the trade name PEBAX®, from ATOMCHEM POLYMERS, Birdsboro, Pa.

In some embodiments, the material of the sheath 10 can be blended with a liquid crystal polymer (LCP). For example, the mixture can contain up to about 5% LCP. This has been found to enhance torqueability. The sheath 10 can be made up of a plurality of outer tubular segments, each segment being made of materials having different durameters to impart varying degrees of flexibility to different sections.

Some examples of suitable metals and metal alloys include nickel-titanium alloy, such as linear elastic or superelastic nitinol, nickel-chromium alloy, nickel-chromiumiron alloy, cobalt alloy, stainless steel, such as 304v stainless steel; or the like; or other suitable material. However, as discussed above, in some embodiments, consideration should be given to the MRI compatibility of the material chosen.

In some embodiments, the introducer sheath may be provided with an initial rigid shape for the area including bends 20, 22 and intermediate section 18, but may be reshaped by a physician before insertion to better match the anatomy of the patient. For example, the bends 20, 22 and intermediate section 18 may be made of a material such as PTFE that is rigid, but may be heated and re-shaped, so that once re-cooled, the bends 20, 22 and intermediate section 18 will retain the new shape.

In some embodiments, the bends 20 and 22 can include or be made of materials, or have structure that renders them more flexible or softer than other portions of the sheath. For example, in some embodiments, the bend 20 can be more flexible or softer than at least a part of the distal portion 24 or than at least a part of the intermediate portion 18. Likewise, in some embodiments, the bend 22 can be more flexible or softer than at least a part of the intermediate portion 18 or than at least a part of the proximal portion 26.

In some embodiments, introducer sheath 10 can be made of or include a lubricious material, for example tetrafluoroethylene, or a copolymer of tetrafluoroethylene with perfluoroalkyl vinyl ether (more specifically, perfluoropropyl vinyl ether or perfluoromethyl vinyl ether), or the like. Also, in some embodiments, the sheath 10 can include a coating, for example a lubricious, a hydrophilic, a protective, or other type of coating may be applied over portions or all of the sheath 10. Hydrophobic coatings such as fluoropolymers provide a dry lubricity which improves guidewire handling and device exchanges. Lubricious coatings can aid in insertion and steerability. Suitable lubricious polymers are well known in the art and may include silicone and the like, hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

It can be appreciated that the sheath 10 can be made of a single layer of material, or a plurality of layers. For example, sheath 10 can be include one or more layers disposed or stacked on top of one another. The different layers may be made of the same material or different materials. In one example, one of the layers may be made of a generally less flexible polymer than the other(s). In another example, one or more of the layers may be made of or doped with an indicator material to enhance imaging. Additionally, in some embodiments, one of the layers may act as a support layer, and can include, for example, a braid, coil, or other such structures. The sheath 10 can be constructed using any appropriate technique, for example, by extrusion, a heat bonding process, casting, molding, and the like.

FIG. 3 is a diagrammatic side view of an illustrative embodiment showing an introducer sheath. Introducer sheath 200 is shown with additional features highlighted at the proximal end 205. The illustrative example includes a non-return valve 207 at proximal end 205. The non-return valve 207 is adapted so that a catheter or other device may be introduced through the valve 207 without allowing fluid within the lumen of introducer sheath 200 to escape, and, conversely, without allowing foreign particles to enter the lumen of introducer sheath 200. For example, the non-return valve 207 may be a hemostatic valve. The non-return valve 207 may include a side port 209 as shown.

Three lengths, L1, L2 and L3, and two angles $\alpha$ and $\beta$ are defined in FIG. 3. L3 corresponds to the proximal segment 210. The length of the proximal segment 210 can be defined as desired, based upon the desired use, entry location, and the anatomy of a patient. For some embodiments, L3 can range from about five to ninety centimeters, though greater and lesser lengths may be used in other embodiments. Proximal segment 210, although shown as a straight segment, may be a flexible member and also can include curves to enable a physician to access the proximal end 205 as needed.

A first angle $\alpha$ is defined at the bend 212 between proximal segment 210 and intermediate segment 215. Angle $\alpha$ can be shaped as desired, based upon the desired use, entry location, and the anatomy of a patient. In some embodiments, a is defined such that at least a portion of the proximal segment 210 can extend along the skin of a patient when the intermediate segment 215 is disposed in an interspace between two vertebrae of a patient. In some embodiments, $\alpha$ may vary in the range of about up to one hundred and seventy degrees; in other embodiments, $\alpha$ is in the range of about thirty to one hundred and seventy degrees. In additional embodiments, $\alpha$ may be more tightly restricted, for example, in some embodiments, $\alpha$ varies in the range of about one hundred and twenty and one hundred and fifty degrees. However, greater and smaller angles are contemplated in some embodiments. Additionally, it should be understood that the first angle $\alpha$ need not be defined in all embodiments. For example, in some embodiments, there may be no angle defined between the proximal segment 210 and intermediate segment 215, such that the proximal segment 210 can extend out of the patient at the same angle as defined by the intermediate segment 215.

Length L2 corresponds to the length of intermediate segment 215. The length of the intermediate segment 215 can be varied as desired, based upon the desired use, entry location, and anatomy of the patient. In some embodiments, the intermediate segment has a length that is adapted to extend from the spinal subarachnoid space to the surface of the skin of a patient through an interspace between two vertebrae of a patient. In some embodiments, the intermediate segment may vary in the range of about two to twelve, four and eight, or five to seven centimeters, although greater and lesser lengths may be possible given a particular patient's anatomy.

A second angle $\beta$ is defined at curve 217 between intermediate segment 215 and distal segment 220. In some embodiments, $\beta$ is defined such that at least a portion of the distal segment 210 can extend along the skin of a patient when the intermediate segment 215 is disposed in an interspace between two vertebrae of a patient. $\beta$ may be chosen as an angle such that when the sheath is placed in the anatomy of a patient, the intermediate section 215 extends through an interspace between two vertebrae of a patient, and the distal segment 220 can extend along the spinal subarachnoid space. In some embodiments, $\beta$ may be in the range of about forty five to one-hundred eighty, or sixty to one-hundred eighty degrees. In another embodiment, $\beta$ may be in the range of about one hundred to one hundred twenty five degrees. In additional embodiments, $\beta$ may be more tightly restricted. For example, in one embodiment, $\beta$ varies in the range of about one-hundred twenty-five and about one-hundred forty-five degrees. β may vary depending upon the interspace chosen for introduction.

Although the illustrative embodiment shows that α and β can add up to approximately one-hundred and eighty degrees, this is not necessarily the case, and the proximal segment 210 and distal segment 220 can be, but will often not be, parallel to one another as shown. In some embodiments, α and β may add up to an angle in the range of about one hundred fifty and two hundred ten degrees. For example, the distal and proximal segments 210, 220 may be flexible members, so that, while the angles α and β may be defined, the actual orientation between the proximal segment 210 and distal segment 220 is not entirely defined by the two angles α and β.

It should also be understood that one or more angles or bends in addition to angles α and β can be defined in the sheath. For example, the proximal shaft 210 can include one or more additional angles of bends such that the proximal segment 210 extends in a desired direction or location. For another example, the distal segment 220 can include one or more additional angles or bends such that it can be adapted to aid in navigation to a desired location in the patient's anatomy.

The illustrative embodiment shown suggests that the introducer sheath is approximately parallel to the patient's spine. In other embodiments, the proximal segment 210 may extend toward the patient's head such that the overall shape of the introducer is approximately a C shape. Alternatively, both the distal and proximal segments 210, 220 could extend away from the patient's head. Also, the proximal segment 210 may extend at some angle away from the spine, for example, the proximal segment could extend toward the left or right (from the patient's perspective), out of line with the spine.

Length L1 corresponds to the distal segment 220, and terminates in distal tip 225. The length of the distal segment 220 can be varied as desired, based upon the desired use, entry location, and anatomy of the patient. In some embodiments, the distal segment 220 has a length that is adapted to extend along the spinal subarachnoid space such that the distal tip 225 is disposed in a desired location in the subarachnoid space for the particular procedure being performed. In some embodiments, length L1 varies in the range of about one to seventy-five centimeters. In other embodiments, length L1 varies in the range of about twenty-five to fifty centimeters. However, greater and lesser lengths may be used given a particular patient's anatomy and the particular needs of the procedure being performed.

In some embodiments, as noted, the distal segment length L1 may be relatively long, over twenty centimeters, while in others, the distal segment length L1 may be as little as one centimeter. One reason for the variation is that the introducer sheath may be introduced for different purposes and at different locations along the spinal subarachnoid space. For example, a long introducer sheath having a distal length L1 of about fifty centimeters could be used for a tall patient, where the introducer sheath is intended to advance through the spinal subarachnoid space from the lumbar region to a location near the pia mater that surrounds the brain. Meanwhile, a shorter introducer sheath having a shorter distal length L1 of about a centimeter may be used where access is desired to a region within the spinal subarachnoid space itself. For example, an operation seeking to filter the CSF of blood may use a short introducer sheath placed near a source of blood that is leaking into the CSF in the spinal subarachnoid space, reducing the length of the spinal subarachnoid space that is subjected to possible irritation caused by incursion and introduction of the distal segment 220.

FIG. 4 is a side view of another illustrative embodiment showing an introducer sheath, this time including alterations to the proximal end. The introducer sheath 300 includes proximal segment 310 that is engaged with an attachment apparatus 312. Bend 314 separates proximal segment 310 from intermediate segment 315, and bend 317 separates intermediate segment 315 from distal segment 320 which ends in distal end 322. The angles and lengths for angles α and β and lengths L1 and L2 may be as discussed above with respect to FIG. 3. However, length L3, corresponding to proximal segment 310, may be changed in the illustrative embodiment. The proximal segment 310 ends in proximal connector 332. As shown, connector 332 may engage with a second connector 338 to form a fluid-sealed proximal section that would include proximal segment 310 and additional segment 330. For example, connector 332 may be a female Leur lock, and second connector 338 may be a male Leur lock adapted to fit with connector 332. The additional segment 330 may be of any length; in one illustrative embodiment it is about thirty centimeters. In another illustrative embodiment, the additional segment 330 is of a length making it possible for a physician to access the proximal end 334 of additional segment 330 from outside an imaging apparatus while a patient is inside the imaging apparatus with the introducer sheath inserted. The proximal segment 310 may also be any suitable length; in one example it is short enough that the connector 332 is integral to attachment apparatus 312. In another embodiment (not shown) the connector 332 may be integral or adjacent to a second attachment apparatus for securing the location of the joint between connector 332 and second connector 338; this may be done to prevent patient motion during an operation from disrupting the interface between connector 332 and second connector 338.

An additional feature shown, but not required for use with the configuration including first connector 332 and second connector 338, is the multi-end nature of additional segment 330, including a Y 335 and multiple adaptors, for example, dual adaptors 336, 337. A similar structure could be used at the proximal end of many of the embodiments described herein. Adaptors 336, 337 may be any of a variety of known manifolds for providing a proximal end to catheters, including, for example, Leur locks, hemostatic valves, and other non-return valves. The length L4 corresponding to added segment 330 may be selected from among a range from about a centimeter up to a meter or even more. In other embodiments, more than one added segment 330 may be included, for example, with each segment having a connector on each end for attaching to additional segments, with a proximal-most segment including an adaptor such as adaptors 336, 337. The added segments may be included to enable an operator to vary the length of the portion of the introducer sheath 300 that extends out from the body of the patient, allowing the operator to access the proximal end 334 of the introducer sheath 300 or the adaptors 336, 337 enabling access to the interior of the introducer sheath from a location distant from the point of entry to the patient.

The segments 310, 315, 320 and including added segment 330, along with connectors 314, 338 and adaptors 336, 337, may be adapted to allow a catheter or other device to pass therethrough, including for example a guidewire, a suction tube, or the like. Likewise, side ports such as the side port 209 shown in FIG. 3 may be added to any point, including connectors 314, 338 and adaptors 336, 337.

Figure 5:
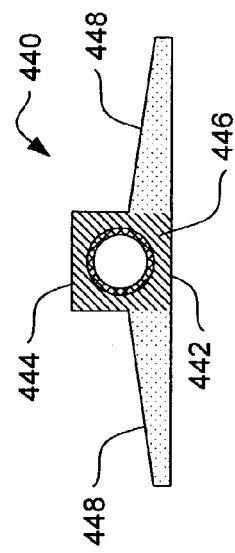
FIG. 5 is a cross sectional view of an illustrative example embodiment of an attachment apparatus including an attachment pad.

FIG. 5 is a cross sectional view of an illustrative embodiment of an attachment apparatus including an attachment pad. Attachment apparatus 400 defines a lumen 402 having an inner diameter ID. Inner diameter ID may vary as required to allow either fixed or slidable engagement with a proximal portion of an introducer sheath as desired. For example, ID may vary in the range of two-tenths of a millimeter up to about five millimeters or more, depending upon the size of the proximal portion of the introducer sheath. As noted above, the proximal portion of the introducer sheath is not limited by the anatomy of the patient in the same way that the intermediate and distal portions may be. Attachment apparatus 400 has a thickness 404 that may vary as needed; in the apparatus 400 as shown, the thickness 404 exceeds the diameter of the lumen 402. In other embodiments, this is not required.

A feature of the attachment apparatus 400 shown in FIG. 5 is that it includes an adhesive pad 406. The adhesive pad 406 may be used to secure the attachment apparatus 400 to the skin or other anatomy of a patient. Any of a wide variety of adhesives commonly used in medical procedures to attach apparatuses to a patient may be included in adhesive pad 406.

Figure 6:
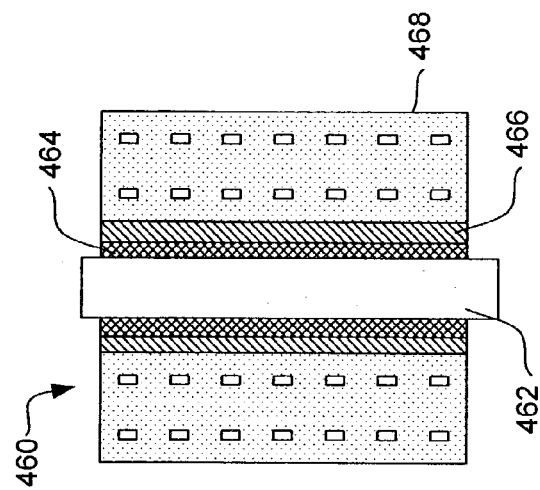
FIG. 6 is an overhead view of an illustrative example embodiment of an attachment apparatus illustrating the relative sizes of various features.

FIG. 6 is an overhead view of an illustrative attachment apparatus displaying the relative sizes of various features. The illustrative attachment apparatus 420 is shown with an elongated device 422. The attachment apparatus 420 has width 424 and length 426, and includes lumen edge 428 and flap 430. Lumen edge 428 may take on several forms, including but not limited to a lubricious material for providing slidable fitting with respect to the elongated device 422; a gap allowing a loose fit with respect to the elongated device; a lubricant or disinfectant coating; and a secure fitting that provides a rigid attachment to the elongated device, for example an adhesive or a keyed joint. The attachment apparatus 420 may have a length 426 in the range of up to about fifty centimeters or longer, and in some embodiments ranges between three and five centimeters. The attachment apparatus 420 may have a width in the range of up to fifty centimeters, and in some embodiments ranges between five and seven centimeters. The attachment apparatus 420 may have a height in the range of about one to fifty millimeters, or more or less.

Although several illustrative embodiments herein display the lumen edge 428 allowing passage of the elongated device 422 in the center of the attachment apparatus 420, in other embodiments the lumen edge 428 may allow the elongated device 422 to pass along the left or right edges of the attachment apparatus, or it may pass diagonally through a rectangular attachment apparatus. Likewise, the shape of the attachment apparatus 420 may include any of a broad variety of shapes, for example, a circle, oval, square, rectangle, or other polygon or like shapes, or combinations thereof.

Figure 7:
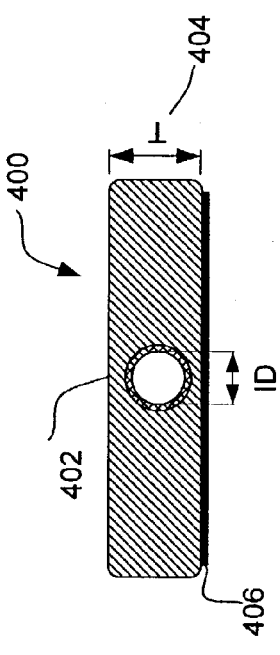
FIG. 7 is a cross sectional view of an illustrative embodiment of an attachment apparatus including attachment flaps.

The lumen edge 428 may include devices for selectably securing the elongated device 422 at a particular longitudinal location. For example, a set screw may be included for compressing the sides and preventing motion of the elongated device 422. Likewise, a compressible coil may be included, where compression of the ends of the coil causes the inner diameter of the coil to increase, allowing a device to pass therethrough, while release of the ends of the coil allows the coil to contract and secure the elongated device. A lever attached to a spring loaded member could be used, where the spring loaded member would press against the elongated device to prevent longitudinal movement of the elongated device unless the lever is lifted, which would release the elongated device. As noted above, the proximal portion of an introducer sheath may include a ridged, ribbed, roughened or otherwise adapted region for enabling a device integral to the lumen edge 428 to prevent or impede longitudinal motion FIG. 7 is a cross sectional view of an illustrative attachment apparatus including attachment flaps. Attachment apparatus 440 includes lumen 442 with lumen edge 444 along with main structure 446 and attachment flaps 448. Attachment flaps 448 may be used to stabilize the attachment apparatus 440 or secure it to the skin of a patient. The main structure 446 is sized and adapted to provide a structure for lumen 442 to pass through, and may include features to allow a device to be slidably or rigidly disposed within lumen 442. Though excluded from the illustrative embodiment shown in FIG. 7, the adhesive pad 406 in FIG. 5 may be included to provide additional securing force, and may be applied beneath the attachment flaps 448, the main structure 446, or both.

Figure 8:
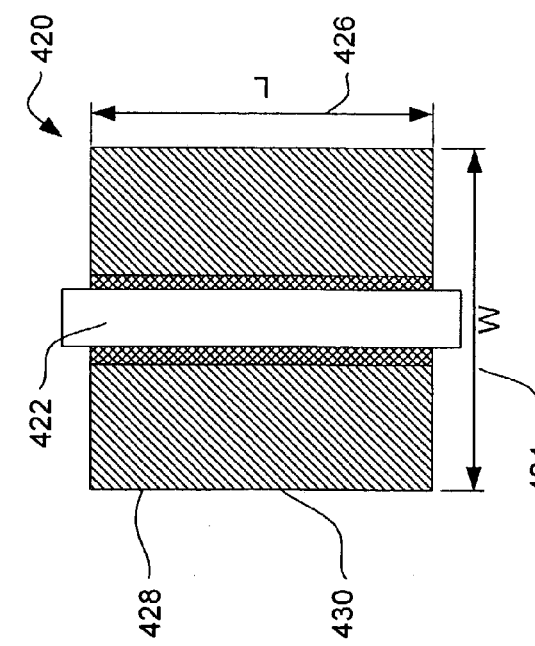
FIG. 8 is an overhead view of an illustrative embodiment of an attachment apparatus including suture hooks.

FIG. 8 is an overhead view of an illustrative attachment apparatus including attachment flaps. In the overhead view of attachment apparatus 460, elongated member 462 is shown through lumen area 464 which is part of main structure 466 having attachment flaps 468 along either side. Attachment flaps 468 are illustrated including attachment holes 470. Attachment holes 470 may be adapted to allow a surgeon to apply sutures to the skin of a patient and stitch the attachment flaps 468 to the patient's skin. Alternatively, attachment holes 470 may be used as access points to apply an adhesive to the patient's skin. In another embodiment, the underside of attachment flaps 468 includes an adhesive layer that adheres to the skin of a patient securely once applied to the skin, but which release when exposed to a solvent or other releasing substance, and the attachment holes 470 are used as access points to apply the solvent or other releasing substance.

Figure 9:
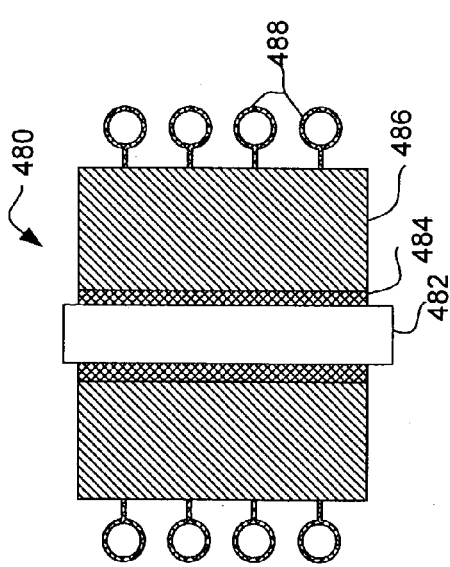
FIG. 9 is an overhead view of an illustrative embodiment of an attachment apparatus including attachment flaps.

FIG. 9 is an overhead view of another illustrative embodiment of an attachment apparatus including suture hooks. In the attachment apparatus 480 of FIG. 9, elongated device 482 passes through lumen area 484, which is part of main structure 486, that is connected to suture hooks 488. The suture hooks 488 may be adapted to allow a surgeon to apply sutures through them and thus stitch the attachment apparatus 480 to the skin of a patient.

Figure 10:
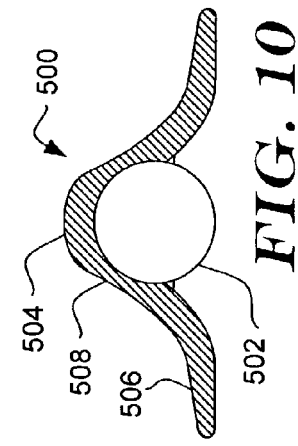
FIG. 10 is a cross sectional view of another illustrative embodiment of an attachment apparatus.

FIG. 10 is a cross sectional view of another illustrative attachment apparatus. The attachment apparatus 500 shows an elongated member 502 going through a cuff 504 which is connected to flaps 506. The elongated member 502 may be separated from cuff 504 by a thin layer 508. The thin layer 508 may in some embodiments be designed to engage the outer surface of elongated member 502 to prevent longitudinal motion. The thin layer 508 may, in an alternative embodiment, be designed to allow elongated member 502 to move easily within the cuff 504. Flaps 506 may include suture holes or sticky or adhesive pads for securing the flaps to the skin of a patient.

Figure 11:
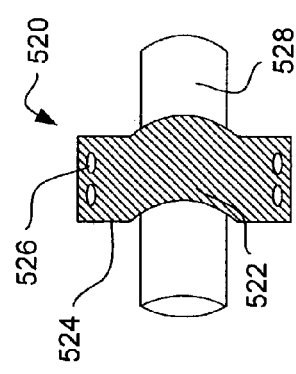
FIG. 11 is an overhead view of an illustrative embodiment of an attachment apparatus similar to that shown in FIG. 10.

FIG. 11 is an overhead view of an illustrative embodiment similar to that shown in FIG. 10. As shown in FIG. 11, attachment apparatus 520 includes cuff 522 connected to attachment flaps 524 including attachment holes 526. Elongate member 528 is shown passing through an opening in cuff 522.

Figure 12:
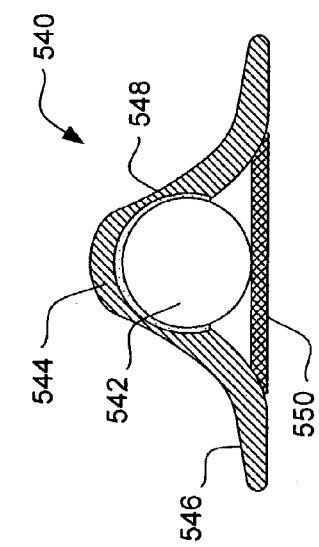
FIG. 12 is a cross sectional view of another illustrative embodiment of an attachment apparatus including a tissue pad.

FIG. 12 is a cross sectional view of another illustrative embodiment of an attachment apparatus including a tissue pad. In FIG. 12, the attachment apparatus 540 shows elongated member 542 passing through cuff 544 which is attached to attachment flaps 546. Cuff 544 includes thin layer 548, which is in contact with elongate member 542. Also in contact with elongate member 542 is tissue pad 550. Attachment flaps 546 may include suture holes or hooks or adhesive pads for securing the attachment apparatus 540 to the skin of a patient.

In some embodiments, the thin layer 548 and elongate member 542 fixedly engage one another, but in other embodiments the elongate member may be longitudinally moved after the attachment apparatus 540 is secured to a patient's skin. Motion of the elongate member 542, if pressed against the patient's skin, could cause irritation or discomfort to the patient. Thus, as shown in FIG. 12, a tissue pad 550 may be included to reduce discomfort caused by rubbing of the elongate member 542 against the patient's skin. An additional advantage of the tissue pad 550 is that, in some embodiments, the side of the tissue pad 550 in contact with the patient's skin may be adapted to adhere to the patient's skin, adding to the attaching force supplied by attachment apparatus 540.

Figure 13:
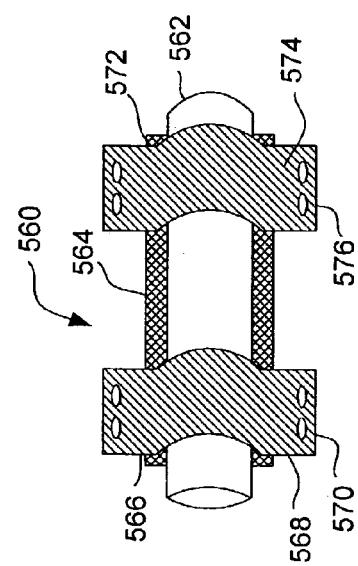
FIG. 13 is an overhead view of an illustrative embodiment of a multi-element attachment apparatus.

FIG. 13 is an overhead view of an illustrative embodiment attachment apparatus integrating multiple securing devices. As shown, attachment apparatus 560 has elongated member 562 passing therethrough, with tissue pad 564 extending a longitudinal distance from first cuff 566 to second cuff 572. The tissue pad 564 may be included to reduce patient discomfort caused by motion of the elongated member 562, and may also include an adhesive surface for application to the skin of the patient. First cuff 566 is connected to first flaps 568 having securing holes 570. Securing holes 570 may be suture holes, for example. Second cuff 572 is connected to second flaps 574 having securing holes 576, which may again include suture holes, for example. The illustrative embodiment shown in FIG. 13 has the advantage of providing greater distance between attachment locations, which may reduce localized skin irritation to the patient, or may allow easier access to one or both cuffs. In one embodiment, the first cuff 566 may be provided proximal of second cuff 572, and first cuff 566 may include a device for selectively preventing longitudinal motion of elongated member 562, while second cuff 572 may allow free longitudinal motion of elongated member 562; for the illustrative embodiment, the first cuff 566 may be located so that a physician can easily access first cuff 566, while the second cuff 572 may provide additional attachment force (side-to-side and vertical attachment) near the entry location into a patient but may not be accessible to the physician, for example, if the patient is inside an MRI machine.

Figure 14:
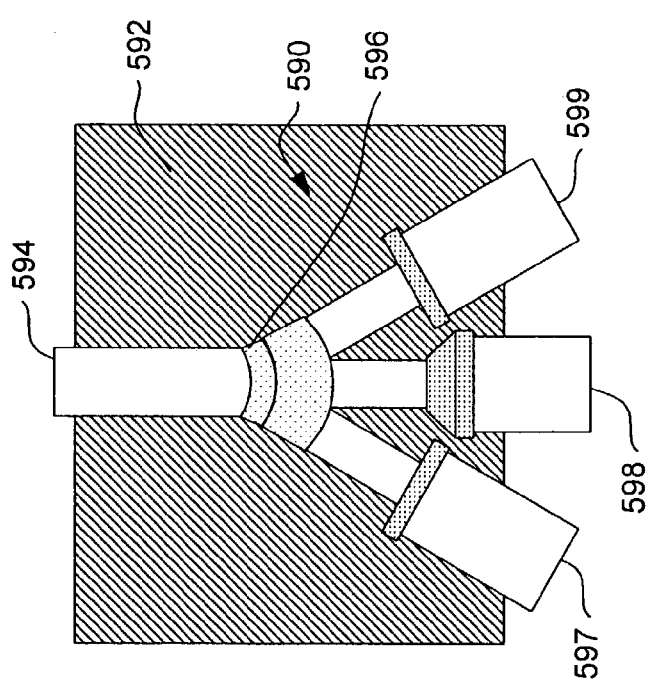
FIG. 14 is an overhead view of an illustrative embodiment of an attachment apparatus including multiple proximal inlets to a distal outlet.

FIG. 14 is an overhead view of an illustrative embodiment attachment apparatus including multiple outlets from a single catheter. As shown, the attachment apparatus 590 includes a main section 592 that has an elongated member portion 594 extending distally and three adaptors 597, 598, 599 extending proximally. A Y joint 596 is included as part of the attachment apparatus 590. The attachment apparatus 590 may be secured to the patient as noted above. The attachment apparatus 590 thus provides a location securing the elongated member portion to the patient's skin and also enables a physician to introduce multiple devices easily at one secured, fixed location. The adaptors 597, 598, 599 may include Leur locks, hemostatic valves, or any other non-return type of valve, for example.

Figure 15:
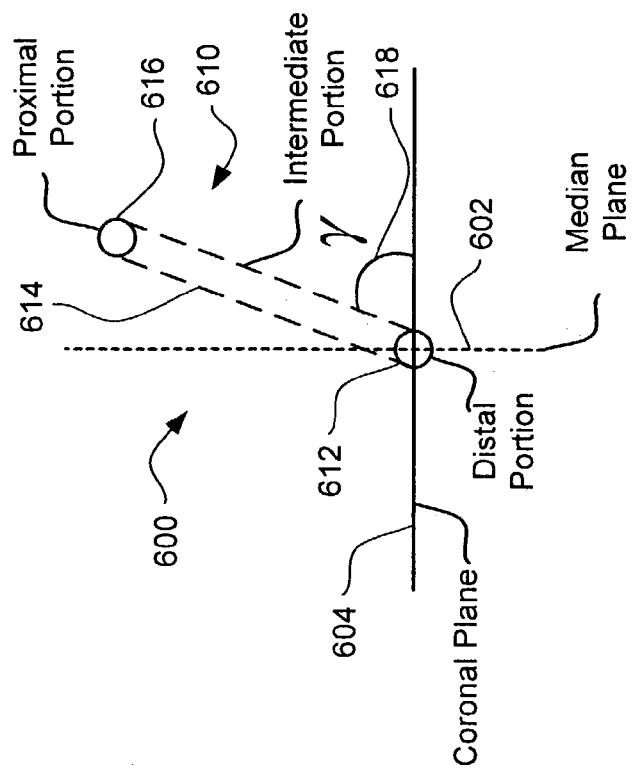
FIG. 15 is a diagrammatic cross sectional view of an illustrative embodiment of an introducer sheath as inserted into a patient highlighting several angles with respect to anatomical planes.

FIG. 15 is a highly diagrammatic cross sectional view of an illustrative introducer sheath as inserted into a patient highlighting several angles with respect to anatomical planes. The median plane 602 and coronal plane 604 are defined for a particular subject. The introducer sheath 610 includes distal portion 612, intermediate portion 614, and proximal portion 616. As shown, the distal portion 612 may run longitudinally (i.e. perpendicular to the paper) along both the median plane 602 and coronal plane 604. This corresponds to the vertebral canal. The angles discussed above with respect to FIGS. 1–3 are given as angles along the median plane between succeeding portions of the introducer sheath. An additional angle can be defined as shown. The angle $\gamma$ 618 is defined as the angle formed along the transverse plane between the intermediate section 614 and the coronal plane, as shown in FIG. 15. The angle $\gamma$ 618 may vary between about 55 and about 125 degrees in some embodiments, while in other embodiments the angle $\gamma$ 618 can be chosen from within the range of about 70 to about 110 degrees.

Figure 16:
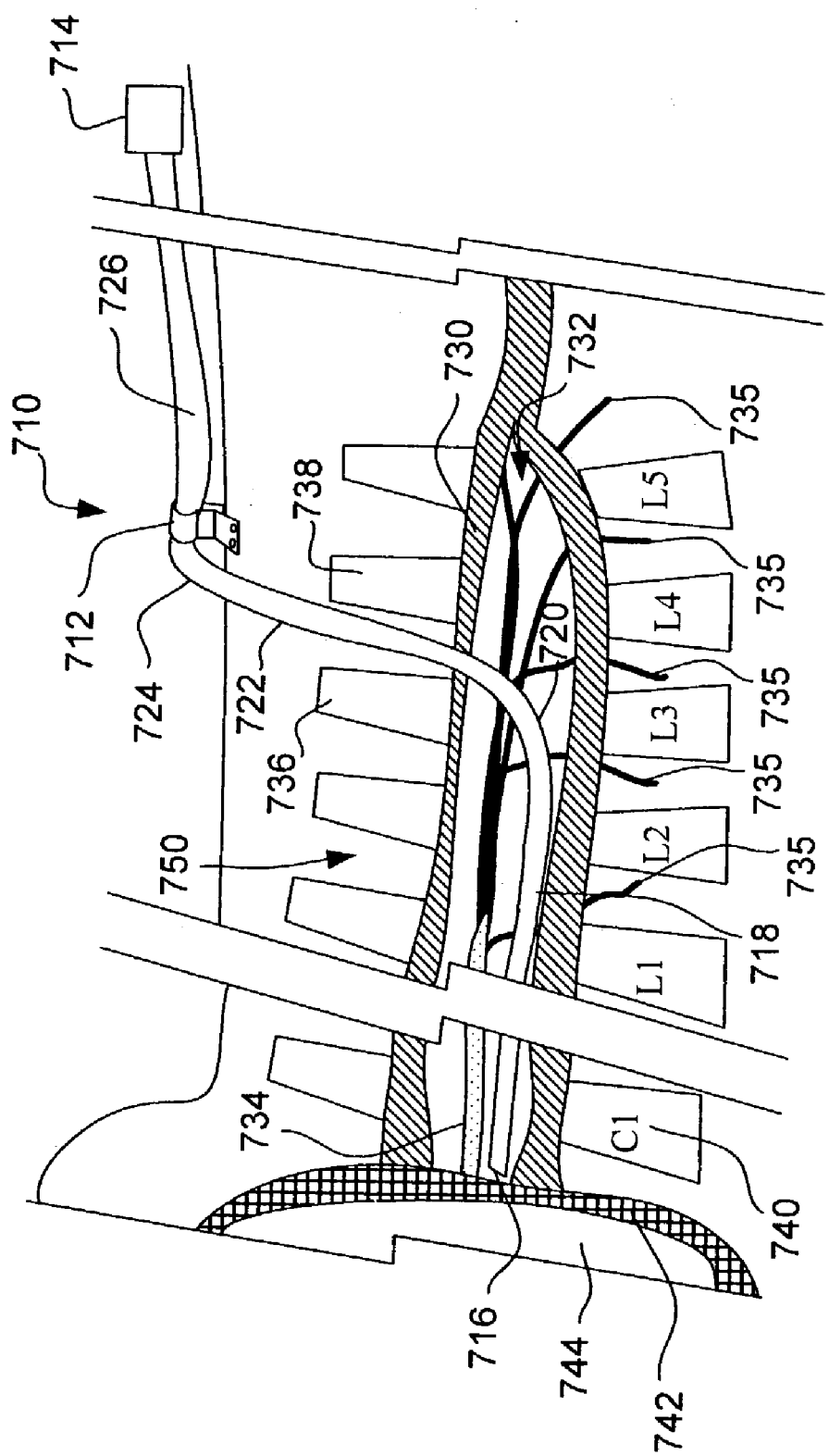
FIG. 16 is a partial side view of an example embodiment of an introducer sheath shown to illustrate the selection of sizes for one embodiment.

FIG. 16 is a partial side view of another embodiment of an introducer sheath shown to illustrate a method of use and selection of sizes. In the embodiment 700 a medical procedure has been undertaken where introducer sheath 710, including attachment apparatus 712, proximal member 714 and distal end 716, has been introduced into a patient. The introducer sheath includes distal portion 718, with first bend 720 connecting to intermediate portion 722, in turn connected to second bend 724 and proximal portion 726. The intermediate portion 722 has been advanced past dural membrane 730 and into subarachnoid space 732 which includes the spinal cord 734 and illustrates several spinal nerves 735. The introduction occurs between two vertebrae 736, 738 identified as L3 and L4. The distal portion 718 is sized so that it extends from the first bend 720 all the way to a location past the first cervical vertebra 740, such that distal end 716 is adjacent to membrane 742 which separates the spinal subarachnoid space 732 from tissue 744. Tissue 744 may, for example, be a portion of the brain, while membrane 742 may be the pia mater, for example.

In an alternative embodiment, rather than sizing the distal portion 718 to achieve the shown and described location for the distal end 716, the entry location may be specifically chosen for a given length of introducer sheath 710 distal portion 718. Thus, for example, if an introducer sheath 710 has distal portion 718 that extends a distance corresponding to the distance from L3 to membrane 742, then the interspace between L3 and L4 (bony structures 736, 738) may be selected for entry instead of an alternative interspace such as the L1–L2 interspace 750.

For several embodiments herein, there is reference to the pia mater, a membrane that surrounds the brain, and may need to be penetrated to access, for example, the ventricles of the brain. During cadaver testing, a tough membrane has been encountered and eventually punctured while attempting to advance a guidewire from an introduction location in the lumbar area into the area of the brain. Several cadaver studies are more fully explained in U.S. patent application Ser. No. 09/905,670, entitled METHODS AND APPARATUSES FOR NAVIGATING THE SUBARACHNOID SPACE, which is incorporated herein by reference. While the cadaver studies did not definitively determine which membrane may have been the tough membrane encountered, it is assumed for purposes of discussion herein that the pia mater is that tough membrane. It may become apparent in the future the exact nature of the tough membrane that had to be pierced, and a membrane other than the pia mater may be identified, for example the membrane of Lilequist, which is identified in application Ser. No. 09/905,670 as one possibility. However, for purposes herein, the pia mater is presented as an illustrative membrane to be pierced in some operations, and it is sufficient for one of skill in the art to note that there may be locations within the subarachnoid and intracranial spaces that may be useful to identify and specifically access with an introducer sheath. Other locations and membranes may be chosen for access without diverting from the spirit of the present invention.

Figure 17:
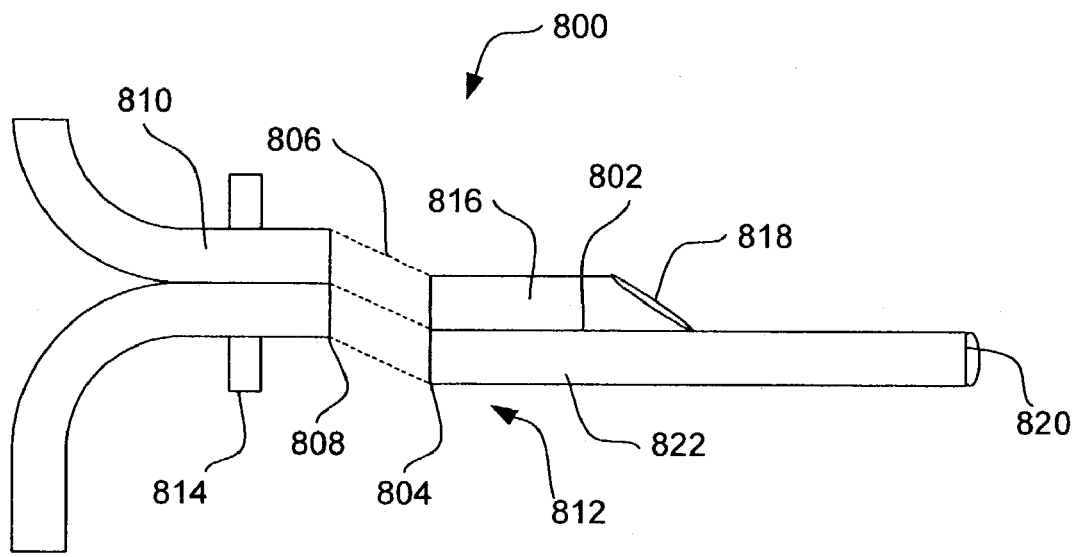
FIG. 17 is a diagrammatic overhead view of an illustrative embodiment of a dual lumen introducer sheath.

FIG. 17 is a diagrammatic overhead view of another illustrative embodiment introducer sheath including multiple lumens. Such an embodiment can be, for example, adapted for use as a CSF exchanger that may be used for cooling an area of the spinal column, for example, or for other functions where multiple lumens may be desirable. The introducer sheath includes a distal portion 802, first bend 804, intermediate section 806, second bend 808, and proximal portion 810. The introducer sheath 800 includes a dual lumen section 812 that corresponds to an area including an attachment apparatus 814, proximal portion 810, second bend 808, intermediate portion 806, and first bend 804. A first lumen 816 terminates in opening 818 occurring proximal the distal end 820 of the introducer sheath 800. Second lumen 822 provides a section that reaches the distal end 820 of the introducer sheath 800.

For use as a CSF cooling device, CSF may be drained from the spinal subarachnoid space using opening 818. One example embodiment may also include passing CSF through first lumen 816 to a pumping device and then to a refrigeration unit that can cool the CSF. After the CSF is cooled in the refrigeration unit, it may be returned to the subarachnoid space via second lumen 822 and delivered at or near distal end 820. For use in a CSF filtration system, for example, the CSF may be pumped in the same manner as above, but rather than passage trough a refrigeration unit, it may pass through a filtration unit to remove impurities, or undesired particles or substances, such as blood. For use as a CSF replacement device, CSF may be drained through one of the two lumens 816, 822 and replaced, for example, with saline, via the other of the two lumens 816, 822. Examples of CSF cooling are discussed in copending U.S. patent application Ser. No. 10/328,560 filed on even date herewith entitled METHODS AND APPARATUSES FOR NAVIGATING THE SUBARACHNOID SPACE, which is incorporated herein by reference.

An additional feature that is not shown which may be included in the introducer sheaths herein is the inclusion of anchoring devices. Such anchoring devices may be included to secure or provide stability to the entry path for other devices enabled by and introducer sheath. Some examples of such anchoring devices are explained in copending U.S. patent application Ser. No. 10/328,373 filed on even date herewith entitled GUIDE CATHETER FOR INTRODUCTION INTO THE SUBARACHNOID SPACE AND METHODS OF USE THEREOF, which is incorporated herein by reference.

Such a multi-lumen sheath could also be used to introduce multiple devices, such as guidewires, catheters and the like, through the separate lumens. In some embodiments, the lumens end at different locations along the length of the sheath, as shown in FIG. 17, but in other embodiments, the distal ends of the lumens can end at the same point.

Figure 18:
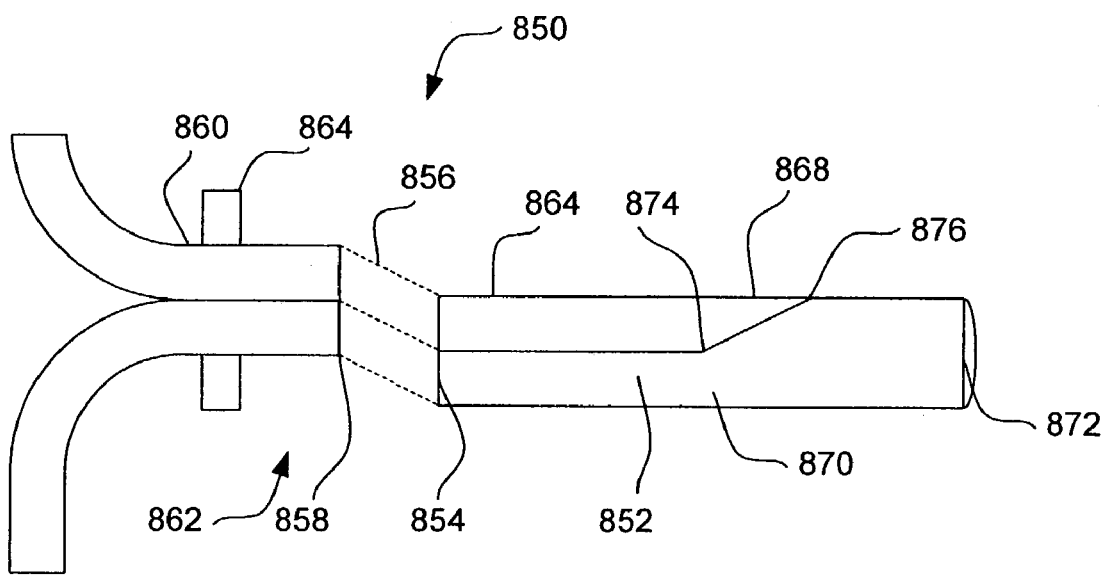
FIG. 18 is a diagrammatic overhead view of one alternative example embodiment to the illustrative example introducer sheath shown in FIG. 17.

FIG. 18 is a highly diagrammatic overhead view of an alternative embodiment to the illustrative introducer sheath shown in FIG. 17. For introducer sheath 850, there is again a distal portion 852, first bend 854, intermediate section 856, second bend 858, and proximal portion 860. The introducer sheath 850 also includes a dual lumen section 862 that corresponds to an area including the attachment apparatus 864, proximal portion 860, first bend 858, intermediate portion 856, and second bend 854. The dual lumen section 862 has first lumen 866 which terminates in opening 868 proximal the distal end 872 of the introducer sheath 850. There is also a second lumen 870 that increases in cross sectional diameter along a region defined by two points 874, 876.

For the illustrative example of FIG. 18, the general operation of the introducer sheath in a CSF cooling, filtration or replacement system the same as above. One difference is that the pressure placed on outflowing fluid coming from the distal end 872 of the insertion sheath is reduced by the increase in the cross sectional area of second lumen 870 between points 874 and 876. Thus, the area directly irrigated by distal end 872 may be protected from damage occurring due to excessive jet-pressure on the exiting fluid.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. An introducer sheath including an elongate shaft having a proximal end and a distal end comprising:
   a first section at the distal end of the elongate shaft;
   a second section proximate the first section;
   a third section proximate the second section;
   wherein the first section and the second section are predisposed at a first angle, and the second section and the third section are predisposed at a second angle;
   an attachment apparatus coupled to the elongate shall adjacent the second angle;
   wherein the first section, the second section, and the third section include a lumen passing therethrough; and
   wherein the first section is adapted for introduction into a spinal subarachnoid space and the first angle, and intermediate section, are adapted for passage through an interspace.

2. The introducer sheath according to claim 1, wherein the second section provides a S-shaped intermediation between the first section and the third section.

3. The introducer sheath according to claim 2, wherein the first section is of a lesser stiffness than the second section and the third section.

4. The introducer sheath according to claim 1, wherein the first angle may be adjusted by warming the material of area of the introducer sheath corresponding to the first angle to a temperature above room temperature.

5. The introducer sheath according to claim 1, wherein the second section has a length in the range of 2–12 centimeters.

6. The introducer sheath according to claim 5, wherein the second section has a length in the range of 5–7 centimeters.

7. The introducer sheath according to claim 1, wherein the first section has a length in the range of 1 and 75 centimeters.

8. The introducer sheath according to claim 7, wherein the first section has a length in the range of 25 and 50 centimeters.

9. The introducer sheath according to claim 1, wherein the third section has a length of at least 5 centimeters.

10. The introducer sheath according to claim 9, wherein the third section has a length of 30 centimeters or less.

11. The introducer sheath of claim 1, wherein the second section has a length that is adapted to separate the first section and the third section such that when the first section is inserted into a subarachnoid space of a patient, at least part of the third section is disposed adjacent the skin of the patient.

12. The introducer sheath according to claim 1, wherein the third section includes a non-return valve.

13. The introducer sheath according to claim 12, wherein the non-return valve is a Leur valve, a hemostatic valve, an injection membrane, or an injection port.

14. The introducer sheath according to claim 1, wherein the first and second sections are adapted for entry into the subarachnoid space of a vertebrate organism.

15. The introducer sheath according to claim 1, wherein the first angle is effected across a length in the range of 0.5–7 centimeters of the first section.

16. The introducer sheath according to claim 15, wherein the first angle is effected across a length in the range of 3–5 centimeters of the first section.

17. The introducer sheath according to claim 1, wherein the first angle is effected across a length of the first section that is more flexible than the rest of the first section.

18. The introducer sheath according to claim 1, wherein the first angle is effected across a length of the first section that is softer than the rest of the first section.

19. The introducer sheath according to claim 1, wherein the second angle is effected across a length in the range of 0.5–7 centimeters of the second section.

20. The introducer sheath according to claim 19, wherein the second angle is effected across a length in the range of 3–5 centimeters of the second section.

21. The introducer sheath according to claim 1, wherein the second angle is effected across a length of the second section that is softer than the rest of the second section.

22. The introducer sheath according to claim 1, wherein the second angle is effected across a length of the second section that is more flexible than the rest of the second section.

23. The introducer sheath of claim 1, wherein a portion of the lumen extending trough the first section has an inner diameter in the range of about 0.1–3 millimeters.

24. The introducer sheath of claim 1, wherein the first section has an outer diameter in the range of 0.2–4 millimeters.

25. The introducer sheath of claim 24, wherein the first section has an outer diameter in the range of 1–4 millimeters.

26. The introducer sheath of claim 1, wherein the attachment apparatus includes a suture location for attaching the attachment apparatus to a patient's skin with a suture.

27. The introducer sheath of claim 1, wherein the attachment apparatus includes an adhesive layer for adhering the attachment apparatus to a patient's skin.

28. The introducer sheath of claim 1, wherein the attachment apparatus defines an attachment lumen through which the third section passes.

29. The introducer sheath of claim 28, wherein the attachment lumen rums in a longitudinal direction of the attachment apparatus, the length of the attachment apparatus is in the range of up to 50 centimeters, the width of the attachment apparatus is in the range of up to 50 centimeters, and the height of the attachment apparatus is in the range of 2–50 millimeters.

30. The introducer sheath of claim 1, wherein the attachment apparatus is adapted to allow the third section to divide into a multi-member segment.

31. The introducer sheath of claim 1, wherein the attachment apparatus includes two or more separate devices each including an attachment mechanism for attachment to the skin of a patient.

32. The introducer sheath of claim 1, wherein the attachment apparatus includes a gap adapted to decrease discomfort caused to a patient by the attachment apparatus.

33. The introducer sheath of claim 1, wherein the attachment apparatus includes a foam pad adapted to decrease discomfort caused to a patient by the attachment apparatus.

34. The introducer sheath of claim 1, further including a fourth section for attaching to the proximal end of the third section, the third section and the fourth section forming a joint therebetween.

35. The introducer sheath of claim 1, wherein the first angle is in the range of 60–180 degrees.

36. The introducer sheath of claim 35, wherein the first angle is in the range of 125–145 degrees.

37. The introducer sheath of claim 1, wherein the second angle is in the range of 30–170 degrees.

38. The introducer sheath of claim 37, wherein the second angle is in the range of 120–150 degrees.

39. The introducer sheath of claim 1, wherein the first section and at least 5 centimeters of the third section lie in planes parallel to the coronal plane of a patient into whom the introducer sheath has been inserted.

40. The introducer sheath of claim 1, wherein the sheath is adapted so that, once introduced into a patient, the first section extends from a chosen entry location for the patient towards the patient's head.

41. The introducer sheath of claim 1, wherein the third section is of a sufficient length to allow a physician to access the proximal end of the introducer sheath while the first section is disposed within the spinal subarachnoid space of a patient while the patient is being imaged in a magnetic resonance imaging system.

42. The introducer sheath of claim 1, wherein the third section includes more than one non-return valve.

43. The introducer sheath of claim 1, wherein the first section includes a coating detectable by a magnetic resonance imaging system.

44. The introducer sheath of claim 43, wherein the coating includes extracellular gadolinium.

45. The introducer sheath of claim 43, wherein the coating includes dysprosium.

46. The introducer sheath of claim 1, wherein the first section is more flexible than the second section.

47. The introducer sheath of claim 1, wherein the distal end of the first section is more flexible than a less-distal portion of the first section.

48. The introducer sheath of claim 1, wherein at least a portion of the elongate shaft is resistant to kinking.

49. The introducer sheath of claim 48, wherein the elongate shaft includes a kink-resistant support member extending for a portion of the elongate shaft.

50. The introducer sheath of claim 1, wherein the distal end of the first section is softer than a less-distal portion of the first section.

51. The introducer sheath of claim 1, wherein the distal end of the first section is softer than at least a portion of the first section, second section, and third section.

52. The introducer sheath of claim 1, wherein the distal end includes an atraumatic tip.

53. The introducer sheath of claim 1, wherein the first section includes at least one temperature sensor for sensing the temperature of an area of the subarachnoid space.

54. The introducer sheath of claim 1, wherein the first section includes at least one pressure sensor for sensing the pressure within an area of the subarachnoid space.

55. The introducer sheath of claim 1, wherein the elongate shaft is adapted to be detectable using X-ray visualization techniques.

56. The introducer sheath of claim 1, wherein at least a portion of the elongate shaft includes a hydrophilic outer surface.

57. The introducer sheath of claim 56, wherein the hydrophilic outer surface is effected by providing a hydrophilic coating over a portion of the elongate shaft.

58. An introducer sheath comprising:
an elongated tubular member;
means for allowing the elongated tubular member to include a first section that is adapted to be disposed in a spinal subarachnoid space of a person, a second section adapted to be disposed in an interspace of a person, a third section adapted to extend externally from the person, the second section and the third section predisposed at an angle, and an attachment apparatus coupled elongated tubular member adjacent the angle.

59. An introducer sheath for use in percutaneous interspinal navigation into a subarachnoid space of a vertebrate organism, the introducer sheath comprising:
an elongated shaft having a proximal end and a distal end, the shaft including a first section at the distal end and a second section proximal to the first section;
the first section and the second section preformed at an angle similar to the angle defined by an interspace between two vertebrae of the organism and the a spinal subarachnoid space of the organism;
a third section coupled to the second section, the third section being preformed at an angle relative to the second section and disposed proximally of the second section; and
an attachment apparatus attached to the shall adjacent to the angle between the second section and the third section.

60. The introducer sheath of claim 59, wherein the first section is adapted and configured for insertion into a spinal subarachnoid space of the organism, and the second section is adapted end configured for insertion into the interspace between two vertebrae of the organism.

61. The introducer sheath of claim 59, wherein the length of the second section is defined by the distance between the spinal subarachnoid space and the skin of the organism.

62. The introducer sheath of claim 59, wherein the angle between the second section and the third section is similar to the angle defined by the interspace between two vertebrae of the organism and the surface of the skin on the back of the organism.

* * * * *

UNITED STATES PATENT AND TRADEMARK OFFICE
CERTIFICATE OF CORRECTION

PATENT NO.       : 7,011,647 B2
APPLICATION NO.  : 10/328349
DATED            : March 14, 2006
INVENTOR(S)      : Phillip D. Purdy et al.

It is certified that error appears in the above-identified patent and that said Letters Patent is hereby corrected as shown below:

Column 20,
Line 29, delete "shall" and insert -- shaft --.

Column 21,
Line 33, delete "trough" and insert -- through --.
Line 51, delete "rums" and insert -- runs --.

Column 24,
Line 7, delete "shall" and insert -- shaft --.
Line 13, delete "end" and insert -- and --.

Signed and Sealed this

Twentieth Day of June, 2006

JON W. DUDAS
*Director of the United States Patent and Trademark Office*